(12) United States Patent
Chae et al.

(10) Patent No.: US 12,402,814 B2
(45) Date of Patent: Sep. 2, 2025

(54) BODY ATTACHABLE UNIT FOR CONTINUOUS BLOOD GLUCOSE MEASUREMENT

(71) Applicant: I-SENS, INC., Seoul (KR)

(72) Inventors: Kyung Chul Chae, Seongnam-si (KR); Hyun Ho Choi, Seoul (KR); Goang Yel Ryu, Goyang-si (KR); Ji Hoon Wang, Goyang-si (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 853 days.

(21) Appl. No.: 17/261,530

(22) PCT Filed: Jun. 21, 2019

(86) PCT No.: PCT/KR2019/007486
§ 371 (c)(1),
(2) Date: Jan. 19, 2021

(87) PCT Pub. No.: WO2020/027434
PCT Pub. Date: Feb. 6, 2020

(65) Prior Publication Data
US 2021/0290117 A1   Sep. 23, 2021

(30) Foreign Application Priority Data

Jul. 31, 2018  (KR) .................. 10-2018-0089337

(51) Int. Cl.
*A61B 5/145*   (2006.01)
*A61B 5/00*   (2006.01)

(52) U.S. Cl.
CPC ........ *A61B 5/14532* (2013.01); *A61B 5/0024* (2013.01); *A61B 5/6846* (2013.01); *A61B 2562/166* (2013.01)

(58) Field of Classification Search
CPC .. A61B 5/1486–14865; A61B 5/14503; A61B 5/14532; A61B 5/145–14546;
(Continued)

(56) References Cited

U.S. PATENT DOCUMENTS

2003/0100040 A1   5/2003  Bonnecaze et al.
2004/0010207 A1*  1/2004  Flaherty ................. A61B 5/157
                                                                                600/573
(Continued)

FOREIGN PATENT DOCUMENTS

JP    2008-506468    3/2008
JP    2010-538745    12/2010
(Continued)

OTHER PUBLICATIONS

Patent Examination Report 1 dated Sep. 7, 2022 for New Zealand Patent Application No. 772734.
(Continued)

*Primary Examiner* — Jennifer Robertson
*Assistant Examiner* — Elina Sohyun Ahn
(74) *Attorney, Agent, or Firm* — WOMBLE BOND DICKINSON (US) LLP

(57) ABSTRACT

The present invention relates to a body attachment unit for continuous blood glucose monitoring, in which a body attachment unit is manufactured so as to be assembled in an applicator, thereby minimizing additional work and allowing attachment of the body attachment unit to a body simply by operation of the applicator. In particular, a wireless communication chip is provided in the body attachment unit to enable communication with an external terminal, thereby
(Continued)

enabling simple and convenient use without additional work of connecting a separate transmitter, and allowing easier maintenance. In addition, activation occurs by a user's operation after the body attachment unit is attached to the body, such that an activation start time can be adjusted to a time appropriate to the user's needs, and activation can occur in a stabilized state, and thereby allowing more accurate blood glucose monitoring.

12 Claims, 37 Drawing Sheets

(58) Field of Classification Search
CPC ........ A61B 5/6846–685; A61B 5/6848; A61B 5/6849; A61B 5/0024; A61B 2562/16–166; A61B 2562/18; A61B 2562/24–247; A61B 5/4839; A61B 5/150206
See application file for complete search history.

(56) References Cited

U.S. PATENT DOCUMENTS

| | | | |
|---|---|---|---|
| 2008/0004512 A1 | 1/2008 | Funderburk et al. | |
| 2009/0076360 A1* | 3/2009 | Brister .................. | A61B 5/1486 204/403.01 |
| 2010/0198034 A1 | 8/2010 | Thomas et al. | |
| 2013/0150691 A1 | 6/2013 | Pace et al. | |
| 2016/0058344 A1 | 3/2016 | Peterson et al. | |
| 2016/0278672 A1 | 9/2016 | Cho et al. | |
| 2017/0231497 A1 | 8/2017 | Brister et al. | |
| 2017/0290546 A1 | 10/2017 | Antonio et al. | |

FOREIGN PATENT DOCUMENTS

| | | |
|---|---|---|
| KR | 10-1773583 | 9/2017 |
| WO | 2018/222009 | 12/2018 |

OTHER PUBLICATIONS

Notice of Allowance dated Feb. 19, 2021 for Korean Patent Application No. 10-2018-0089337 and its English translation from Global Dossier.
Notice of Allowance dated Jun. 9, 2022 for European Patent Application No. 19 844 101.6.
Decision to Grant dated Oct. 20, 2022 for European Patent Application No. 19 844 101.6.
Notice of Allowance dated Jul. 26, 2022 for Japanese Patent Application No. 2021-503123 and its English translation from Global Dossier.
Office Action dated May 17, 2022 for Japanese Patent Application No. 2021-503123 and its English translation from Global Dossier.
Extended European Search Report dated Aug. 18, 2021 for European Patent Application No. 19844101.6.
Office Action dated Jan. 11, 2022 for Japanese Patent Application No. 2021-503123 and its English translation from Global Dossier.
Office Action dated May 29, 2020 for Korean Patent Application No. 10-2018-0089337 and its English translation by Google Translate.
Office Action dated Dec. 28, 2020 for Korean Patent Application No. 10-2018-0089337 and its English translation from Global Dossier.
Examination Report dated Nov. 1, 2021 for Australian Patent Application No. 2019313138.
International Preliminary Report on Patentability (Chapter I) for PCT/KR2019/007486 issued on Feb. 2, 2021 and its English translation from WIPO (now published as WO2020/027434).
International Search Report for PCT/KR2019/007486 mailed on Sep. 19, 2019 and its English translation from WIPO (now published as WO2020/027434).
Written Opinion of the International Searching Authority for PCT/KR2019/007486 mailed on Sep. 19, 2019 and its English translation by Google Translate (now published as WO2020/027434).
Office Action dated Oct. 3, 2023 for Japanese Patent Application No. 2022-134454 and its English translation provided by Applicant's foreign counsel.
Notice of Allowance dated Mar. 19, 2024 for Japanese Patent Application No. 2022-134454 and its English translation from Global Dossier.

* cited by examiner (a)

(b)

(a)

(b)

(a)

(b)

(a)

(b)

BODY ATTACHABLE UNIT FOR CONTINUOUS BLOOD GLUCOSE MEASUREMENT

CROSS-REFERENCE TO RELATED APPLICATIONS

The present application is the U.S. National Phase of PCT Application No. PCT/KR2019/007486 filed on Jun. 21, 2019, which claims the priority to Korean Patent Application No. 10-2018-0089337 filed on Jul. 31, 2018, the entire contents of which are incorporated herein by reference.

TECHNICAL FIELD

The present disclosure is related to a body attachable unit for continuously measuring blood glucose. In more detail, the present disclosure is related to a body attachable unit for continuous blood glucose measurement in which, by manufacturing in a state that the body attachable unit is assembled in an applicator, the body attachable unit can be attached to a human body by simply operating the applicator by minimizing additional work, specially, by including a wireless communication chip in the body attachable unit in order to provide telecommunication with an external terminal, it is possible that the use can be more simple and convenient without additional work for connecting a separate transmitter and the maintenance can also be more easily performed, and by initiating the operation according to the manipulation of the user after the body attachable unit is attached to the human body, the operation start time can be adjusted to a proper time depending on the need of the user, the operation can be started in a stable status and more precise blood glucose measurement can be provided.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

Additionally, the blood-collecting glucose monitoring system performs the glucose measurement by collecting blood by pricking a pain-sensitive fingertip with a needle by the diabetes patients themselves, and therefore, the blood collecting process may cause pain and aversion. To minimize such pain and aversion, research and development regarding the CGMSs, which can continuously measure glucose levels by inserting a needle-shaped sensor into a portion of the human body, such as the belly or an arm, which is less pain sensitive, have been undertaken, and furthermore, research and development of non-invasive glucose monitoring systems for measuring glucose without collecting blood have been actively undertaken.

Over the past 40 years, non-invasive glucose monitoring systems have been studied regarding various methods of measuring glucose without collecting blood, for example, optical methods, electrical methods, exhalation measurement methods, and the like. *Cygnus* Corporation, Redwoo City, Calif., U.S.A, has developed and launched the Glucowatch® G2 Biographer, a wrist watch type, using reverse iontophoresis, but the sales of this product were stopped in 2007, because of many problems, such as skin stimulation issues and qualification approval issues, malfunction caused by sweating, and low reliability in measurement of hypoglycemia comparing with hyperglycemia. Although a variety of non-invasive glucose monitoring techniques have been introduced and reported to date, there have been no practical uses due to low reliability or accuracy.

A continuous glucose monitoring system includes a sensor module attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, the most of the continuous glucose monitoring systems are manufactured and distributed as a type that a one-time use sensor module is attached to the human body using an applicator, the user should perform multistage operations/manipulation to operate the applicator to attach the one-time use sensor module to the human body, and after the sensor module is attached to the human body, the user should perform various follow-up operations, such as a procedure of withdrawing a needle by the user.

For example, many operations of unpacking the one-time use sensor module, accurately inserting the one-time use sensor module into the applicator, operating the applicator and inserting the sensor module into the skin in a state that the sensor module is inserted to the applicator, after the insertion, withdrawing the needle of the sensor module from the skin using a separate device, and so on should be performed, and in order to transmit the measurement results regarding glucose to a user terminal, the operation of connecting a separate transmitter to the sensor module and any other appropriate operation should be performed.

Accordingly, the operations of measuring glucose using the continuous glucose monitoring systems may be significantly difficult and inconvenient, which are problematic. Additionally, because the operations of the sensor module and the transmitter is not initiated by the user, there may be problems, for example, low accuracy of the blood glucose measurement result and short device lifespan.

SUMMARY

Technical Problem

The present disclosure is invented to solve problems in conventional technique, and the purpose of the present disclosure is for providing a body attachable unit for continuous blood glucose measurement in which, by manufacturing in a state that the body attachable unit is assembled in an applicator, the body attachable unit can be attached to a human body by simply operating the applicator by minimizing additional work, specially, by including a wireless communication chip in the body attachable unit in order to provide telecommunication with an external terminal, it is possible that the use can be more simple and convenient without additional work for connecting a separate transmitter and the maintenance can also be more easily performed.

Another purpose of the present disclosure is for providing a continuous blood glucose measurement apparatus in which, by initiating the operation according to the manipulation of the user after the body attachable unit is attached to the human body, the operation start time can be adjusted to a proper time depending on the need of the user, and the operation can be started in a stable status and more precise blood glucose measurement can be provided.

Solution to Problem

According to an embodiment of the present disclosure, a body attachable unit for continuous glucose measurement, the body attachable unit configured to be insertedly attachable to a body by an applicator for the continuous glucose measurement, the body attachable unit may comprise a housing, wherein a bottom surface of the housing is to contact a skin; a printed circuit board (PCB) disposed inside the housing; a sensor unit installed to the housing, wherein one end portion of the sensor unit outwardly protrudes from the bottom surface of the housing to be inserted into the body when the housing contacts the skin, and an other end portion of the sensor unit is configured to be contacted to electric contact points; and a contact point connecting module included in the housing, the contact point connecting module configured to operate so that the other end portion of the sensor unit and the electric contact points of the PCB contact each other according to manipulation of a user.

In this embodiment, the contact point connection module may be movably disposed between the other end portion of the sensor unit and the electric contact points to block contact between the other end portion of the sensor unit and the electric contact points, and may be configured to release from blocking the contact between the other end portion of the sensor unit and the electric contact points by moving according to the manipulation of the user.

Additionally, the electric contact points of the PCB elastically may protrude in a direction contactable with the other end portion of the sensor unit, wherein the electric contact points of the PCB are configured to be elastically movable by elastic force to contact the other end portion of the sensor unit as the contact point connecting module releases from blocking the contact between the other end portion of the sensor unit and the electric contact points.

Further, the contact point connection module may comprise a movable plate movably disposed between the other end portion of the sensor unit and the electric contact points in the housing, the movable plate configured to be movable from a first location to a second location according the manipulation of the user, wherein a penetrating hole is formed at one side of the movable plate to pressurize the electric contact points toward the PCB at the first location and release from pressurizing the electric contact points at the second location.

Additionally, the housing may comprise a stopper configured to limit a movable range of the movable plate from the first location to the second location.

Further, the movable plate may be configured that a position of the movable plate is fixed in a state that the movable plate is moved to the second location.

Additionally, a locking hook may be formed at one end portion of the movable plate, an interlocking projection configured to be interlocked with the locking hook in a state that the movable plate is moved to the second location may be formed at the housing, and the movable plate may be configured that the position of the movable plate is fixed at the second location by interlockingly coupling the locking hook to the interlocking projection.

Advantageous Effects of Invention

According to an embodiment of the present disclosure, by manufacturing in a state that the body attachable unit is assembled in an applicator, the body attachable unit can be attached to a human body by simply operating the applicator by minimizing additional work, specially, by including a wireless communication chip in the body attachable unit in order to provide telecommunication with an external terminal, it is possible that the use can be more simple and convenient without additional work for connecting a separate transmitter and the maintenance can also be more easily performed.

Additionally, by initiating the operation according to the manipulation of the user after the body attachable unit is attached to the human body, the operation start time can be adjusted to a proper time depending on the need of the user, and the operation can be started in a stable status and more precise blood glucose measurement can be provided.

DETAILED DESCRIPTION OF EMBODIMENTS

Figure 1:
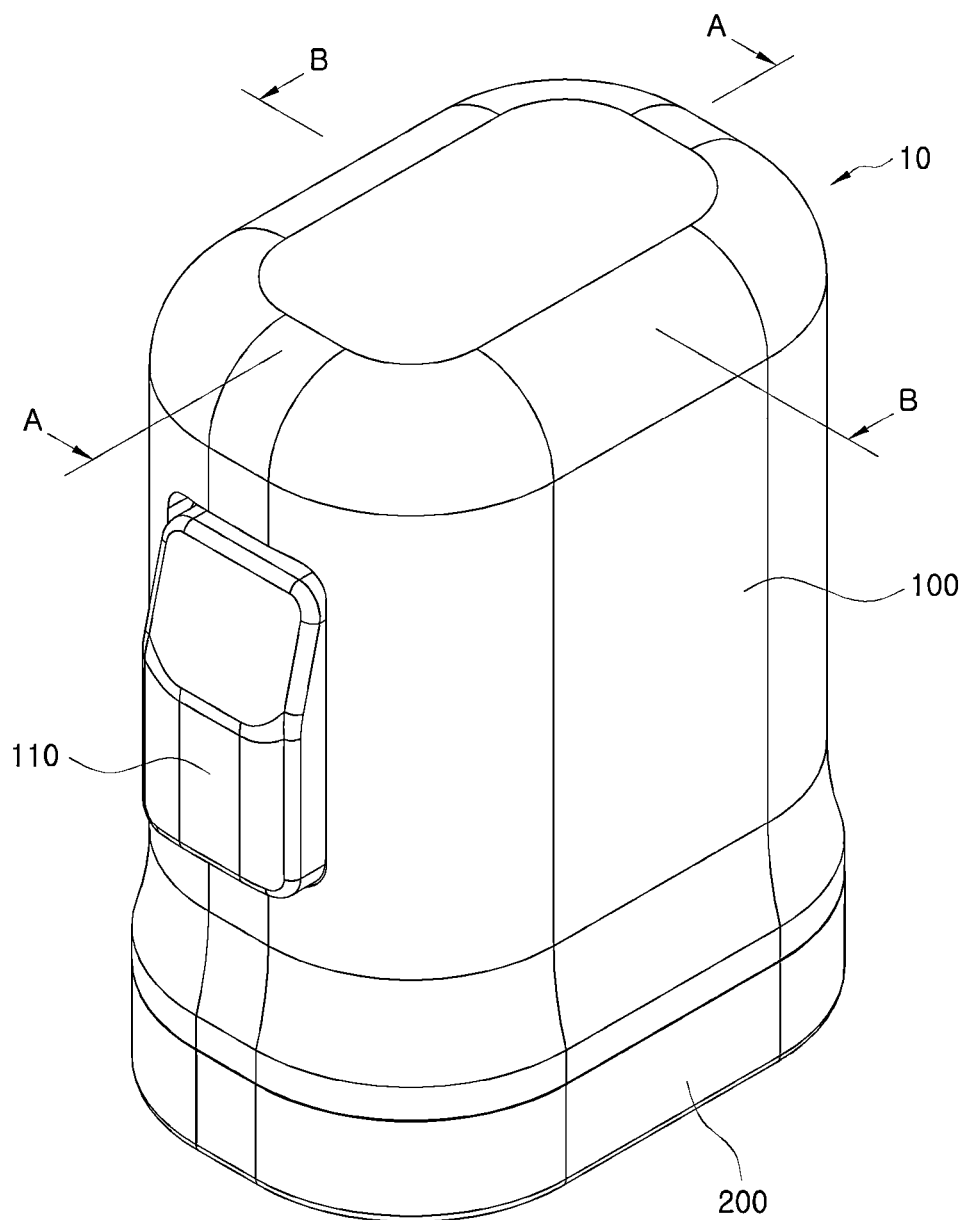
FIG. 1 is a perspective view of schematically illustrating an outer structure of a continuous blood glucose measurement apparatus according to an embodiment of the present disclosure.

Hereinafter, embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known functions and components incorporated herein will be omitted in the case that the subject matter of the present disclosure may be rendered unclear thereby.

Figure 2:
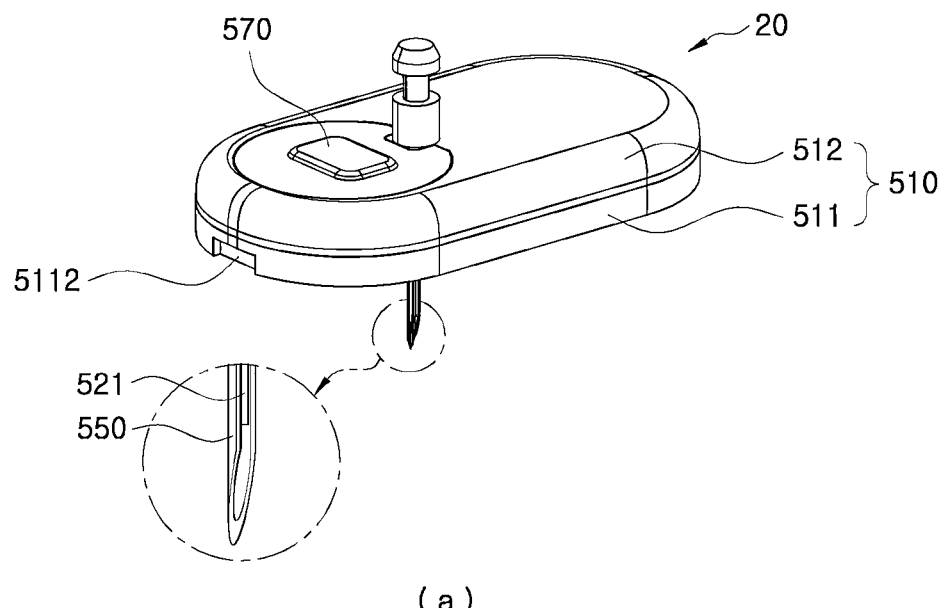
FIG. 2 is a perspective view of schematically illustrating an outer structure of a body attachable unit according to an embodiment of the present disclosure.
Figure 2:
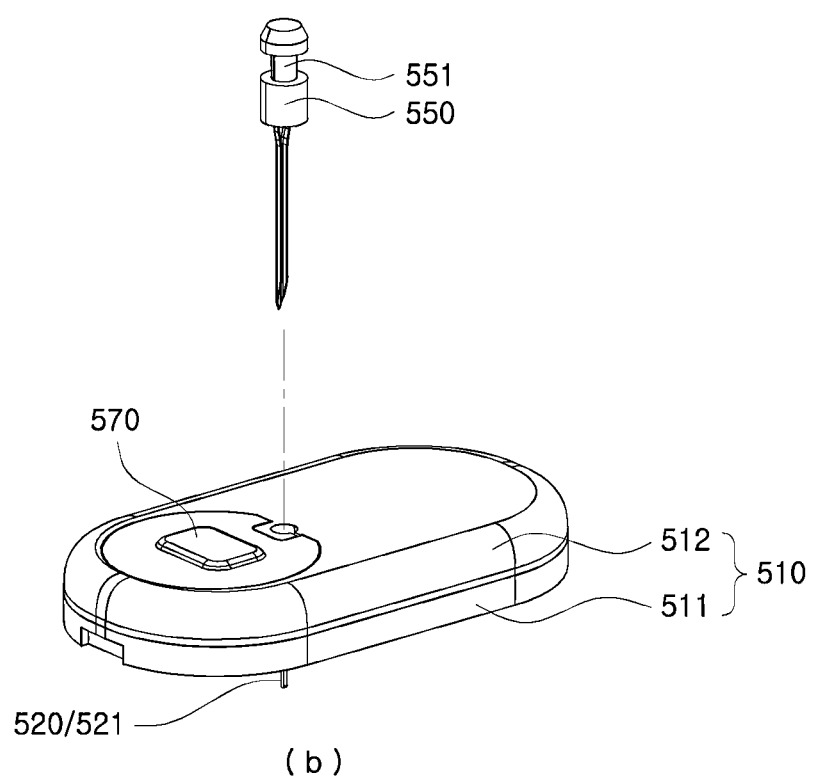
Figure 3:
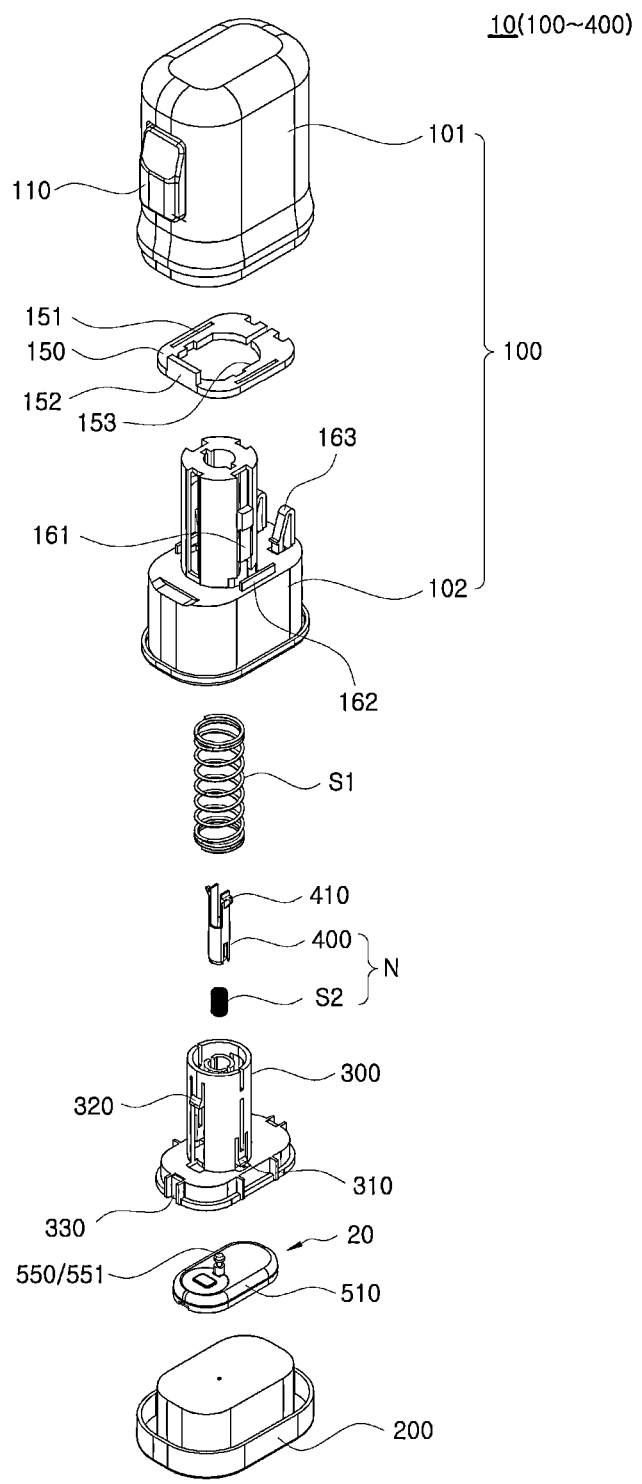
FIG. 3 is an exploded perspective view of the continuous blood glucose measurement apparatus according to an embodiment of the present disclosure.
Figure 4:
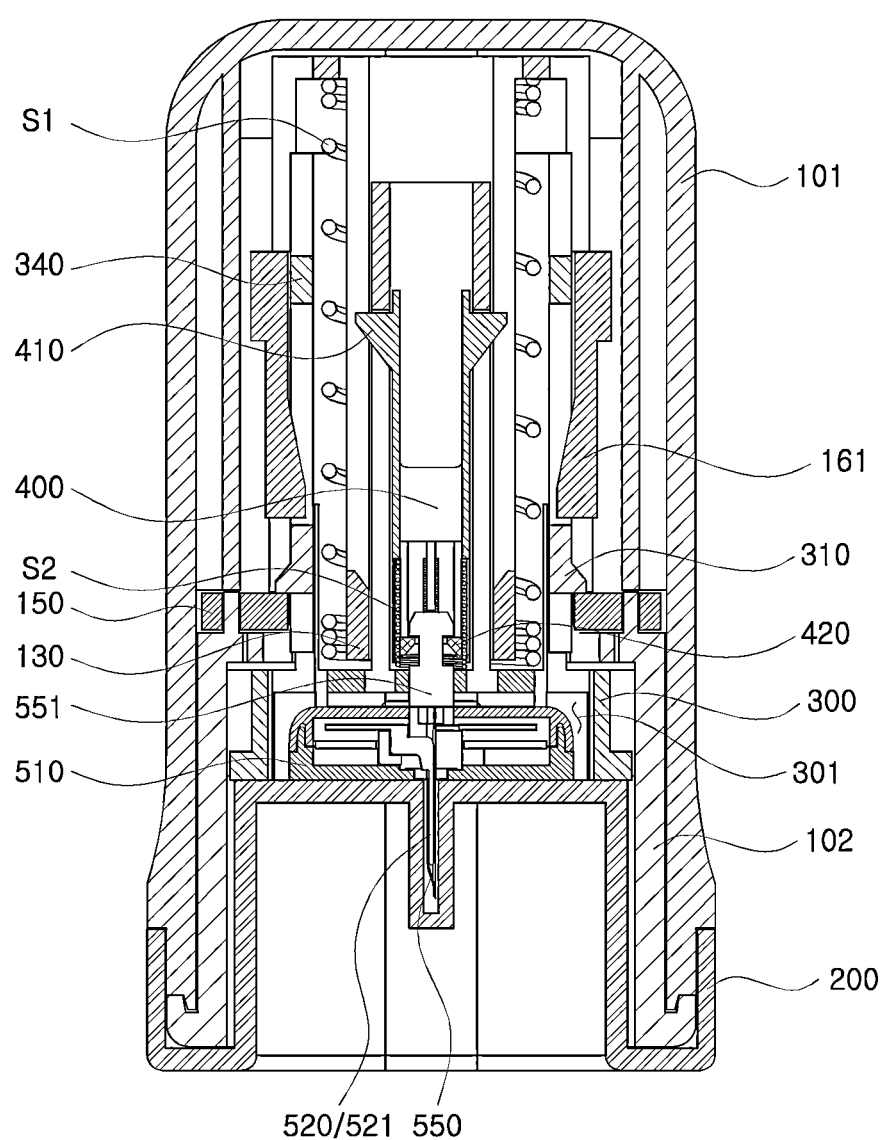
FIG. 4 is a cross-section view taken along line "B-B" of FIG. 1.
Figure 5:
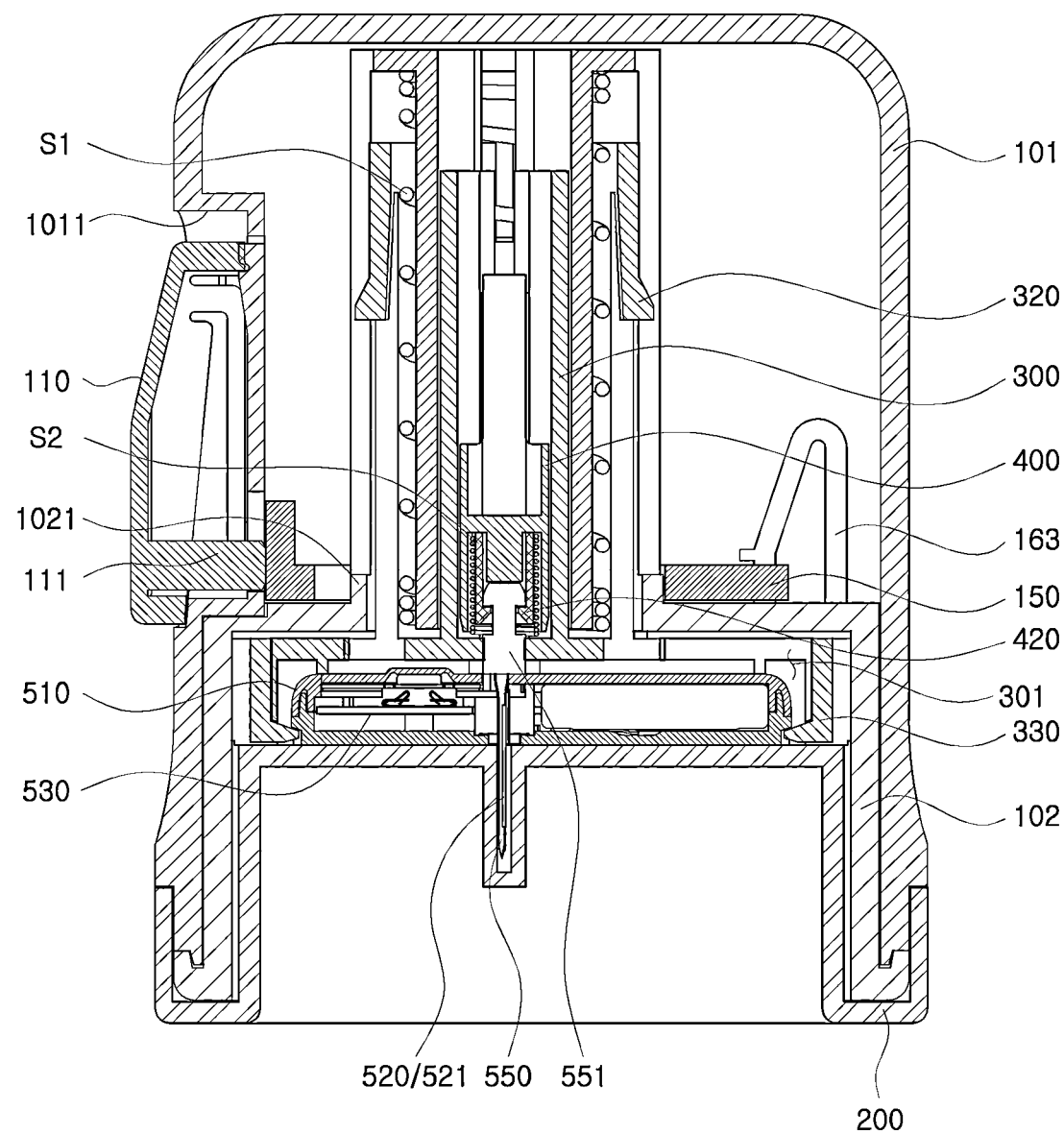
FIG. 5 is a cross-section view taken along line "A-A" of FIG. 1.

FIG. 1 is a perspective view schematically illustrating an outer structure of a continuous blood glucose measurement apparatus according to an embodiment of the present disclosure, and FIG. 2 is a perspective view schematically illustrating an outer structure of a body attachable unit according to an embodiment of the present disclosure, FIG. 3 is an exploded perspective view of the continuous blood glucose measurement apparatus according to an embodiment of the present disclosure, FIG. 4 is a cross-section view taken along line "B-B" of FIG. 1, and FIG. 5 is a cross-section view taken along line "A-A" of FIG. 1.

According to an embodiment of the present disclosure, a continuous blood glucose measurement apparatus may be manufactured as one single unit product that a body attachable unit (20) is assembled inside an applicator (10), and has a simpler structure which can be easily used by minimizing additional work of a user when using the continuous blood glucose measurement apparatus.

The body attachable unit (20) may be configured to be attachable to a human body to periodically measure blood sugar level or glucose by extracting body fluid, and transmit the blood glucose measurement result to an external device such as an external terminal (not shown) and so on. A sensor unit (520) of which one end portion can be inserted into the human body and a wireless communication chip (540) (see FIG. 27) configured to wirelessly communicate with the external terminal can be disposed inside the body attachable unit (20), and therefore, the body attachable unit (20) can be used without additional connection of a separate transmitter.

The applicator (10) is formed such that the body attachable unit (20) is fixedly coupled to inside of the applicator (10), and the applicator (10) is configured to outwardly discharge the body attachable unit (20) according to the manipulation of the user.

In this embodiment, the body attachable unit (20) is assembled and produced in a state that the body attachable unit (20) is inserted into the inside of the applicator (10), and is configured to move in an outward discharge direction pursuant to the operation of the applicator (10) by the manipulation of the user and be attached to the human body.

Therefore, the sensor applicator assembly (1) according to an embodiment of the present disclosure is assembled and manufactured in a state that the body attachable unit (20) is inserted in the inside of the applicator (10) at the manufacturing stage and the body attachable unit (20) can be attached to a skin by only the operation of the applicator (10), and because the sensor applicator assembly (1) is suppled to the user in this state, the user can easily attach the body attachable unit (20) to the skin by only the manipulation simply activating the applicator (10) without extra additional operation for attaching the body attachable unit (20) to the skin. Specifically, since the body attachable unit (20) has the wireless communication chip (540), no connection with an extra transmitter is needed and therefore it can be used more conveniently.

In a conventional continuous blood glucose measurement apparatus, after removing a body attachable unit, which is separately packaged, precisely inserting it into an applicator, and then operating the applicator, the body attachable unit is attached to a skin, but the work precisely inserting the body attachable unit into the applicator is cumbersome as well as difficult and there is a problem in lowering the accuracy of blood glucose measurement because of contaminating the body attachable unit when young children or elderly adults perform this procedure.

In an embodiment of the present disclosure, at the manufacturing stage, it is manufactured and distributed in a state that the body attachable unit (20) is inserted in the applicator (10), and therefore the step that the user removes the body attachable unit (20) from the package and inserts it into the applicator (10) may be omitted, because the body attachable unit (20) can be attached to the skin by simply manipulating the applicator (10), the usability may be significantly improved, and specifically, the accuracy of blood glucose measurement may be improved by preventing the contamination of the body attachable unit (20).

Since it is manufactured in a state that the body attachable unit (20) is inserted in the applicator (10), the body attachable unit (20) and the applicator (10) can be preferably used one time only, not reusable. For this impossibility of the reusable structure, according to an embodiment of the present disclosure, the body attachable unit (2) is configured not to be re-insertable after the body attachable unit (20) inserted in the inside of the applicator (10) is externally discharged.

Therefore, the applicator (10) is formed to be open at one side and the body attachable unit (20) is outwardly discharged through the open side of the applicator (10) to the outside of the applicator (10), and if the body attachable unit (20) is externally discharged by a first one time operation of the applicator (10), it is configured that the body attachable unit (20) cannot be inserted by the user so that another body attachable unit (20) cannot be inserted into the applicator (10) and used after that.

Meanwhile, a separate and additional protection cap (200) can be separably coupled to the applicator (10) in order to block external exposure in a state that the applicator (10) is inserted in the inside of the applicator (10), and it may be configured that the user can attach the body attachable unit (20) to the human body by operating the applicator (10) only after the protection cap (200) is separated.

In the embodiment of the present disclosure, an adhesive tape (560) is provided at a side of the body attachable unit (20) contacting the human body to be attached to the body, to protect the adhesive tape (560) a release paper (561) is attached to a surface of the adhesive tape (560) contacting the human body, and the release paper (561) of the adhesive tape (560) may be configured to be separated and removed from the adhesive tape (560) during the operation of separating the protection cap (200) from the applicator (10).

For example, the release paper (561) may be configured to adhere one side of the release paper (561) to the protection cap (200), and therefore, if the user separates the protection cap (200) from the applicator (10), the release paper (561) may be separated and removed from the adhesive tape (560) together with the protection cap (200). Accordingly, if the user separates the protection cap (200), the release paper (561) of the adhesive tape (560) is separated and removed, and therefore in this status the body attachable unit (20) can be attached to the human body by the operation of the applicator (10).

Additionally, in a state that the body attachable unit (20) is inserted in the inside, the applicator (10) fixes the body the attachable unit (20), and in a state that the body attachable unit (20) is outwardly discharged and moved, the applicator (10) is configured to release the fixed state of the body attachable unit (20). Accordingly, in a state that the body attachable unit (20) is assembled to be inserted in the inside of the applicator (10), the body attachable unit (20) maintains the fixed state, and when the body attachable unit (20) is externally discharged and attached to the skin by actuating the applicator (10), the state fixed between the applicator (10) and the body attachable unit (20) is released, and therefore if the applicator (10) is separated in this state the applicator (10) is separated from the body attachable unit (20) and only the body attachable unit (20) remains on the skin.

Meanwhile, the body attachable unit (20) according to an embodiment of the present disclosure is configured to cause the sensor unit (520) and the wireless communication chip (540) to initiate their operations through a separate switching means controlled by the user. Accordingly, after inserting and attaching the body attachable unit (20) to the human body by using the applicator (10), the user may initiate to operate the body attachable unit (20) through the switching means or other appropriate means included in the body attachable unit (20), and from the time of the initiation of the operation the sensor unit (520) and the wireless communication chip (540) may be operated, the blood glucose of the human body may be measured, and the measurement result may be transmitted to the external terminal. In this embodiment, the switching means operated by the user may be implemented in various ways, and the detailed description of such a switching means and the body attachable unit (20) will be described later with reference to FIGS. 26 to 37.

Additionally, in the body attachable unit (20), the sensor unit (520) is disposed in a housing (510) which is formed to be capable of separating into an upper housing (512) and a lower housing (511), and one end portion of the sensor unit (520) outwardly protrudes from the housing (510) so that it can be inserted and attached to the human body. The sensor unit (520) may comprise a sensor probe unit (521) to be inserted into the human body, and a sensor body unit (522) disposed inside the housing (510), and the sensor probe (521) and the sensor body unit (522) are formed as one end portion and another end portion of the sensor unit (520), respectively, and in a bent shape.

In this embodiment, to smoothly perform the body insertion process of the sensor unit (520), a separate needle unit (550) may be separatably coupled to the housing (510). The needle unit (550) may surround one end portion of the sensor unit (520) and be configured to be inserted together with the sensor unit (520) so that one end portion of the sensor unit (520) can be stably inserted into the human body.

As shown in FIG. 2, the needle unit (550) may be separatably coupled to the housing (510) in a direction penetrating the top and bottom of the housing (510) of the body attachable unit (20), the needle unit (550) may be formed to have a structure covering the outside of the sensor unit (520), and a need head (551) is formed at the upper end portion of the needle unit (550). If the body attachable unit (20) is moved in the direction outwardly discharged by the applicator (10), the needle unit (550) is inserted into the human body first before the sensor unit (520) is inserted into the human body and the needle unit (550) may support the sensor unit (520) such that the sensor unit (520) can be stably inserted in the skin. The needle unit (550) may be coupled with a needle extracting body (400) of the applicator (10) through the needle head (551), and after the body attachable unit (20) is inserted and attached to the human body by the operation of the applicator (10), the needle unit (550) may be configured to be withdrew and removed from the human body by the needle extracting body (400) of the applicator (10).

Next, the details of components of the applicator (10) according to an embodiment of the present disclosure will be followed.

The applicator (10) according to an embodiment of the present disclosure may comprise a main case (100), wherein a pressure button (110) configured to perform pressure operation by the user is installed at one side of the main case (100), a plunger body (300) coupled to a first location of the inside of the main case (100) and configured to be decoupled from the first location by the operation of the pressure button (110) and linearly move from the first location to a second location in an outward discharge direction, and a plunger elastic spring (S1) configured to apply an elastic force to the plunger body (300) so that the plunger body (300) can linearly move from the first location and the second location, and the body attachable unit (20) is coupled with one side of the plunger body (300) and the body attachable unit (20) is configured to be moved together with the plunger body (300) from the first location to the second location.

As discussed above, the protection cap (200) as a separate element may be separatably coupled to the lower end portion of the main case (100) to protect the inside of the body attachable unit (20).

Figure 6:
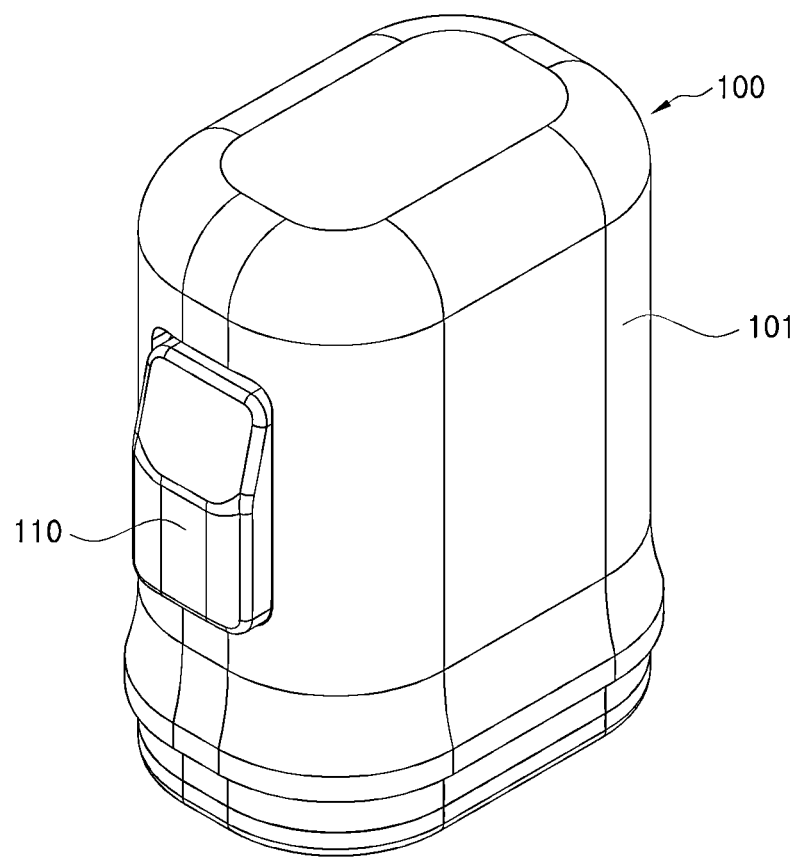
FIG. 6 is an exploded perspective view of schematically illustrating configuration of a protection cap according to an embodiment of the present disclosure.
Figure 6:
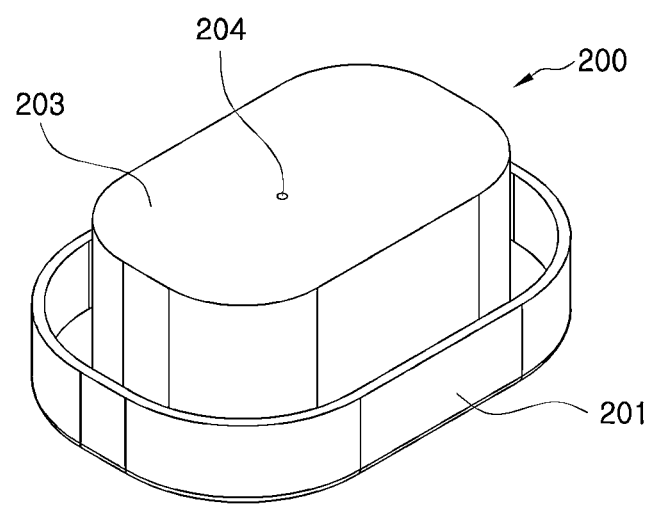
Figure 7:
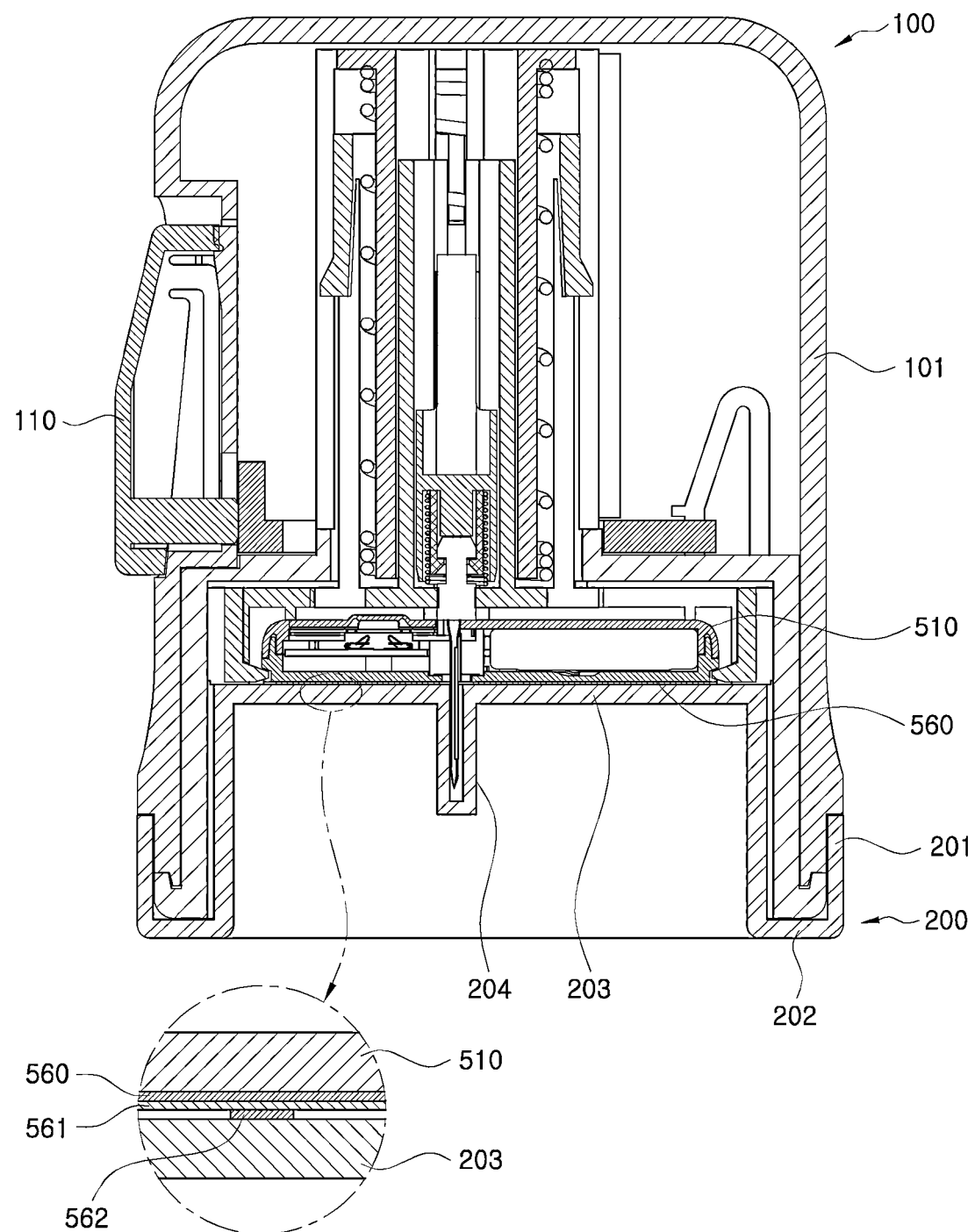
FIGS. 7 and 8 are views of illustrating operations for removing and separating a release paper as well as a protection cap according to an embodiment of the present disclosure.
Figure 8:
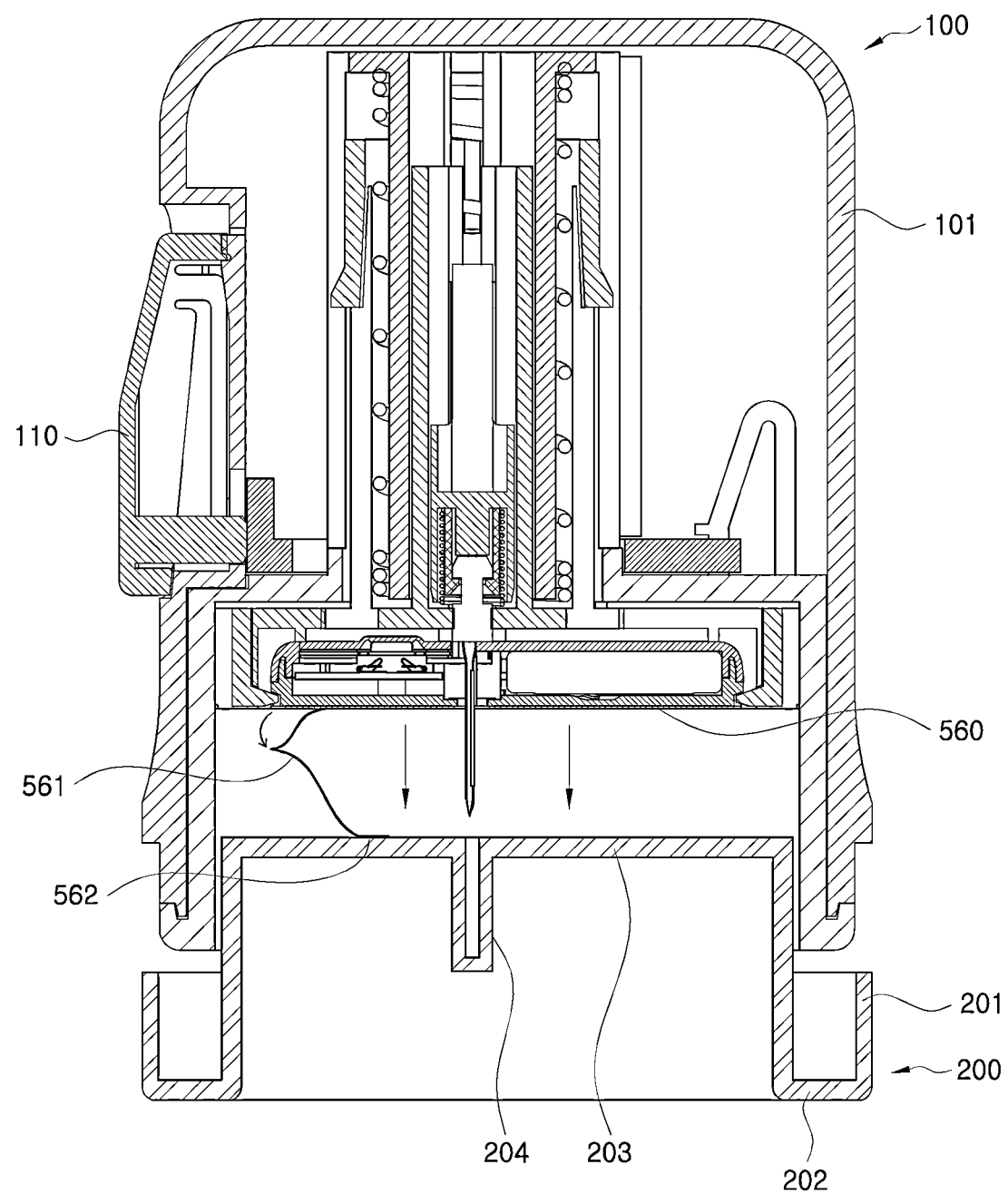

As illustrated in FIGS. 6 to 8, the protection cap (200) may comprise an outer side cover unit (201) covering and contacting an outer circumferential surface of the applicator (10) and formed to be coupled with one end portion of the applicator (10), an extension unit (202) extending from one end of the outer side cover unit (201) in a direction toward the inner center of the applicator (10), and an inner side supporting unit (203) upwardly extending from the extension unit (202) and configured to support a surface of the body attachable unit (20) contacting the human body inserted in the inside of the applicator (10). In this embodiment, at the center portion of the inner side supporting unit (203), the sensor protection unit (204) may be formed to partially downward-protrude to surround a sensor probe (521) downwardly protruding from a surface of the body attachable unit (20) contacting the human body and the needle unit (550).

Accordingly, the protection cap (200) can block the outside exposure of the body attachable unit (20) inserted in the inside of the applicator (10) as well as perform the function of supporting the body attachable unit (20), and may improve the overall structural stability of the applicator.

Meanwhile, as shown in FIGS. 7 and 8, the adhesive tape (560) and the release paper (561) are attached to a surface of the body attachable unit (20) which is to be contacted with the human body, and the release paper (561) of the adhesive tape (560) is configured to be separated and removed from the adhesive tape (560) together with the protection cap (200) in the process of separating the protection cap (200) from the applicator (10).

In this embodiment, the release paper (560) may be applied to the upper surface of the inner side supporting unit (203) of the protection cap (200), and may be attached to the inner side supporting unit (203) of the protection cap (200) through separate adhesive material (562). Accordingly, as illustrated in FIG. 7, the separate adhesive material (562) is adhered to one side of the lower surface of the release paper (561), and this adhesive material (562) is disposed between the upper surface of the inner side supporting unit (203) of the protection cap (200) and the release paper (561) and the lower surface of the adhesive material (562) is adhered to the upper surface of the inner side supporting unit (203). The adhesive strength of the adhesive material (562) may be greater than the adhesive strength between the release paper (561) and the adhesive tape (560). Accordingly, if the protection cap (200) is separated from the applicator (10), the release paper (561) adhered to the inner side supporting unit (203) of the protection cap (200) is also separated together with the protection cap (200) through the adhesive material (562) and separated and removed from the adhesive tape (560).

In this embodiment, at the release paper (561), two cutting lines (not shown) separated with a separation distance identical to a width of the adhesive material (562) are formed to be parallel to each other at some sections, and therefore, as illustrated in FIG. 8, in the process of separating the protection cap (200), the release paper (562) is separated and removed away from the adhesive tape (560) along the cutting lines together with the adhesive material (562) first and then as the separation operation of the protection cap (200) is being performed, i.e., the protection cap (200) keeps being downwardly moved with reference to a direction shown in FIG. 8, a portion of the release paper (562) except the cutting lines is pulled and separated and removed from the adhesive tape (560). By this operation of separating and removing the release paper, the separation-removal operation of the release paper (561) may be smoothly and stably performed.

The pressure button (110) is installed at the main case (100) for pressure operation by the user, and a shooting plate (150) configured to be movable according to the pressure operation of the pressure button (110) may be movably coupled to the inside of the main case (100).

The plunger body (300) may be configured to be coupled and interlocked with the shooting plate (150) and fixed at the first location, and to be released from the interlock with the shooting plate (150) according to the movement of the shooting plate (150) and be moved to the second location by the elastic force of the plunger elastic spring (S1).

The main case (100) may comprise an outer case (101), wherein the pressure button (110) is installed to one side of the outer case (101), and an inner case (102) coupled at the inside of the outer case (101) and configured to guide a linear movement path of the plunger body (300), and the shooting plate (150) may be configured to be movable while being supported in the inner case (102).

Figure 9:
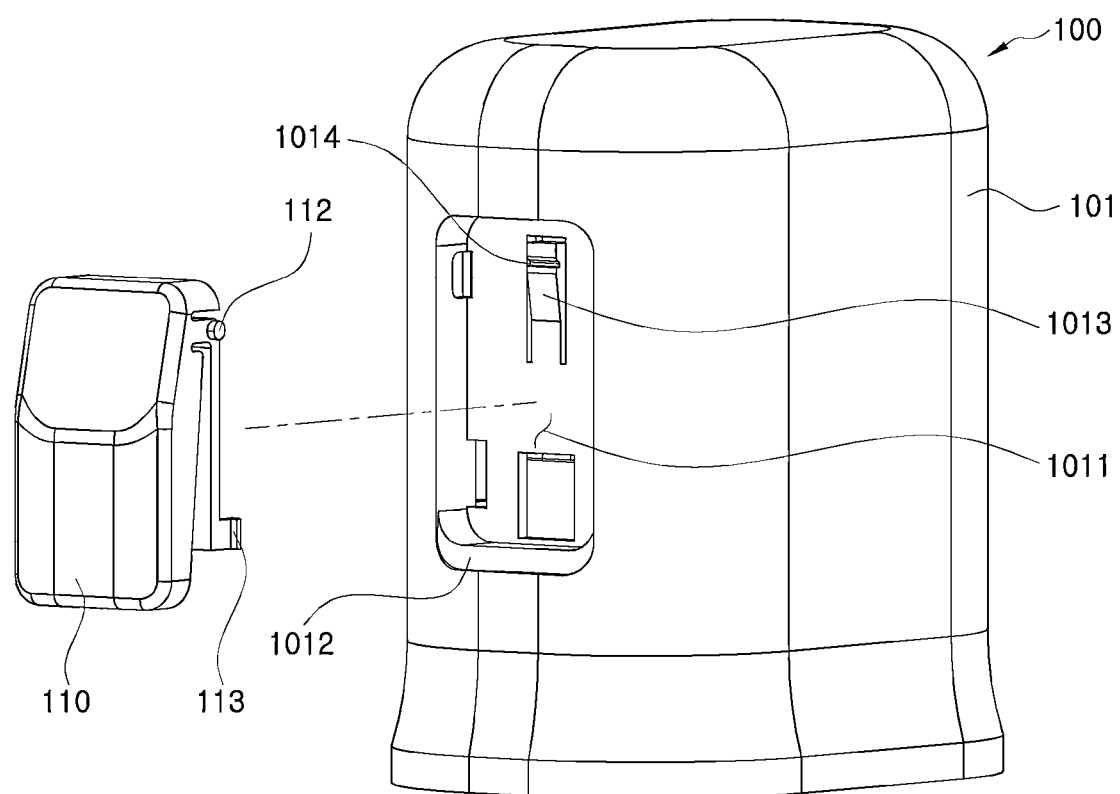
FIG. 9 is a perspective view of schematically illustrating a coupling structure of a pressure button according to an embodiment of the present disclosure.

The pressure button (110) is coupled to the outer case (101) in order to be capable of performing the operation of applying pressure, and as shown in FIG. 9, a button guide groove (1011) is formed at the outer case (101) so that the pressure button (110) can be coupled in order to be capable of performing the operation of applying pressure. The pressure button (110) is configured to be capable of the pressure operation by a structure that a portion of the pressure button (110) is configured to be rotatable around a hinge axis (112) formed at an upper end portion of the pressure button (110), a pressure rod (111) is formed at a lower end portion of the pressure button (110) to apply the pressure to the shooting plate (150), and a separate fixing hook (113) is formed at one side of the pressure button (110) to prevent separation and removal of the pressure button (110).

The pressure button (110) is installed to be configured to provide mode change between a safe mode blocking the pressure movement performed according to the pressure operation and a pressure standby mode capable of performing the pressure movement performed according to the pressure operation.

The pressure button (11) may be configured to, in a safe mode state, slidingly move along an exterior surface of the main case (100) for a certain section to change to a standby mode state. A hanging raised part (1012) is formed at a portion of the main case (100) where the pressure button (110) is coupled, in the safe mode state, the pressure button (110) is interlocked with the hanging raised part (1012) to block the pressuring movement, and as the sliding movement is from the safe mode state to the pressure standby mode state performed, the interlock from the hanging raised part (1012) is released to make the pressuring movement possible.

Figure 10:
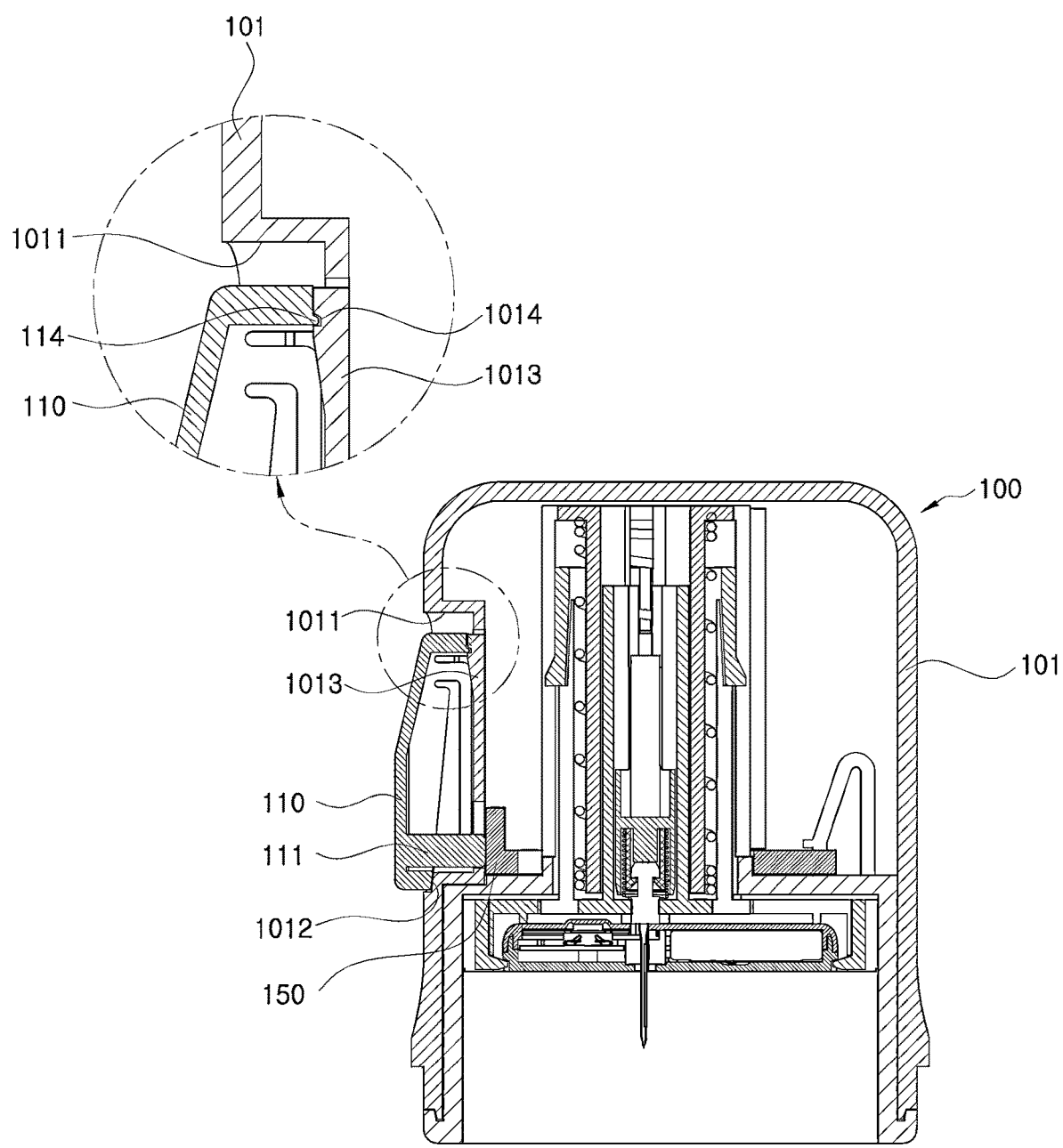
FIGS. 10 and 11 are views of schematically illustrating mode change structures of a pressure button according to an embodiment of the present disclosure.
Figure 11:
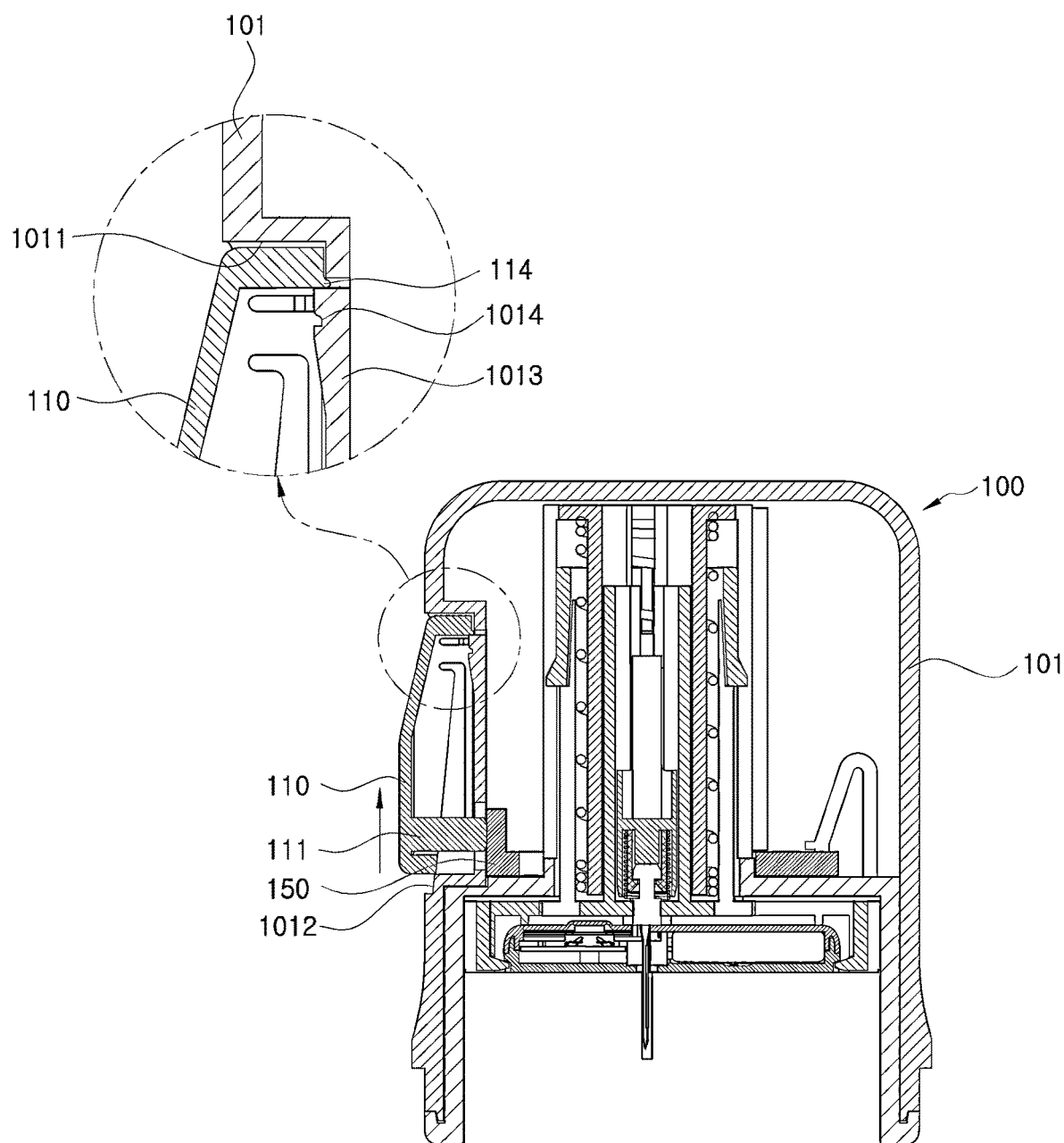

Accordingly, as illustrated in FIG. 10, in the safe mode state, the pressure button (110) is interlocked at the hanging raised part (1012) of the outer case (101) so that the pressurizing operation cannot be performed, and as illustrated in FIG. 11, when the pressure button (110) is upwardly moved to the pressure standby mode state, the interlock with the hanging raised part (1012) of the outer case (101) is released and it is possible to perform the pressurizing operation.

If the pressure button (110) in the safe mode state is slidingly moved to the pressure standby mode, the position of the pressure button (110) may be fixed not to return to the safe mode state.

For this, a fixing protrusion (114) is formed at one side of the pressure button (110), a transformable cut portion (1013) is formed at the bottom surface of the button guide groove (1011) of the outer case (101) and in a structure that a certain section is cut to be elastically transformable, the transformable cut portion (1013) comprises a receivable groove (1014) configured to be insertedly receive the fixing protrusion (114) when the pressure button (110) is positioned at the safe mode, and in a state that the movement of the pressure button (110) to the pressure standby mode is completed, an end portion of the pressure button (110) is interlocked with the fixing protrusion (114) to block the returning movement of the pressure button (110).

In such a structure, the pressure button (110) can perform pressurizing operation by manipulated by the user only in a state that it is slidingly moved to the pressure standard mode state, and therefore the pressure operation caused by the user's mistake can be prevented and it is possible to use safely.

Figure 12:
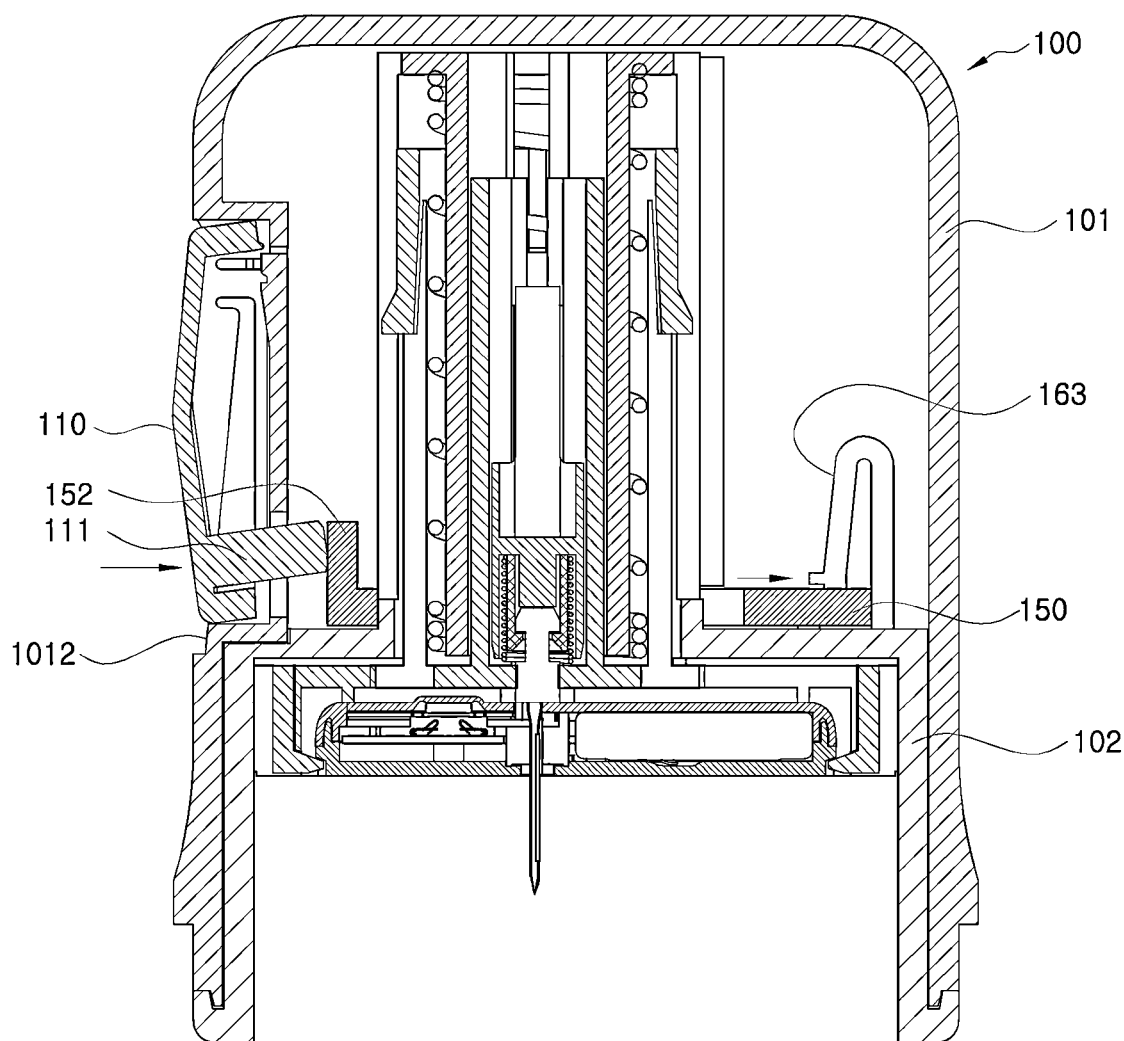
FIG. 12 is a view of schematically illustrating a pressurizing operation state of a pressure button according to an embodiment of the present disclosure.

If the pressure button (110) is changed to the pressure standby mode state and the pressurizing operation is performed as shown in FIG. 12, the pressure button (110) the pressure rod (111) of the pressure button (110) applies pressure to and moves the shooting plate (150).

The shooting plate (150) is supported in the inner case (102) and slidably movably coupled according to the pressurizing operation of the pressure button (110), and the plunger body (300) is interlocked with the shooting plate (150) at the first location and according to the movement of the shooting plate (150) the interlock with the shooting plate (150) is released and the plunger body (300) is moved to the second location by the elastic force of the plunger elastic spring (S1).

Figure 13:
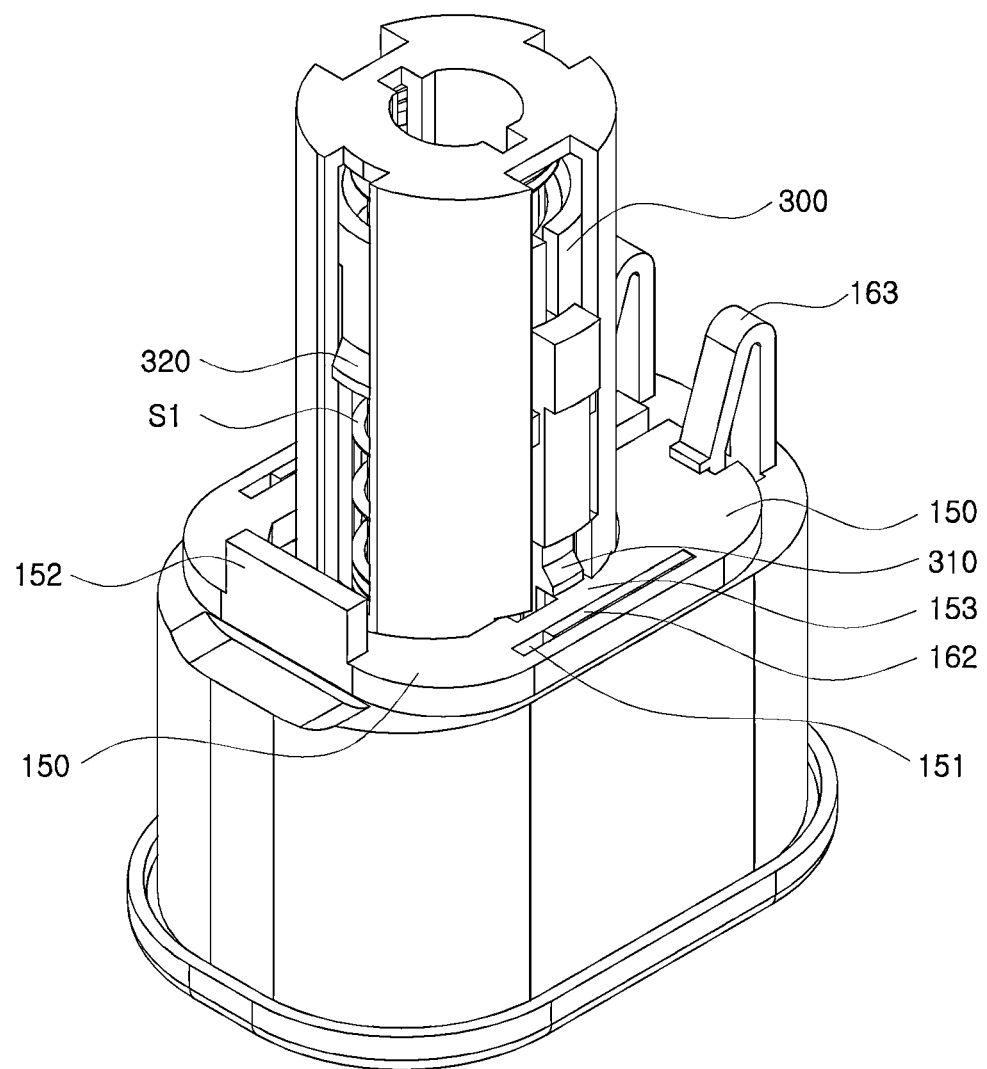
FIGS. 13 and 14 are perspective views of schematically illustrating movement states of a shooting plate caused by operations of a pressure button unit according to an embodiment of the present disclosure.
Figure 14:
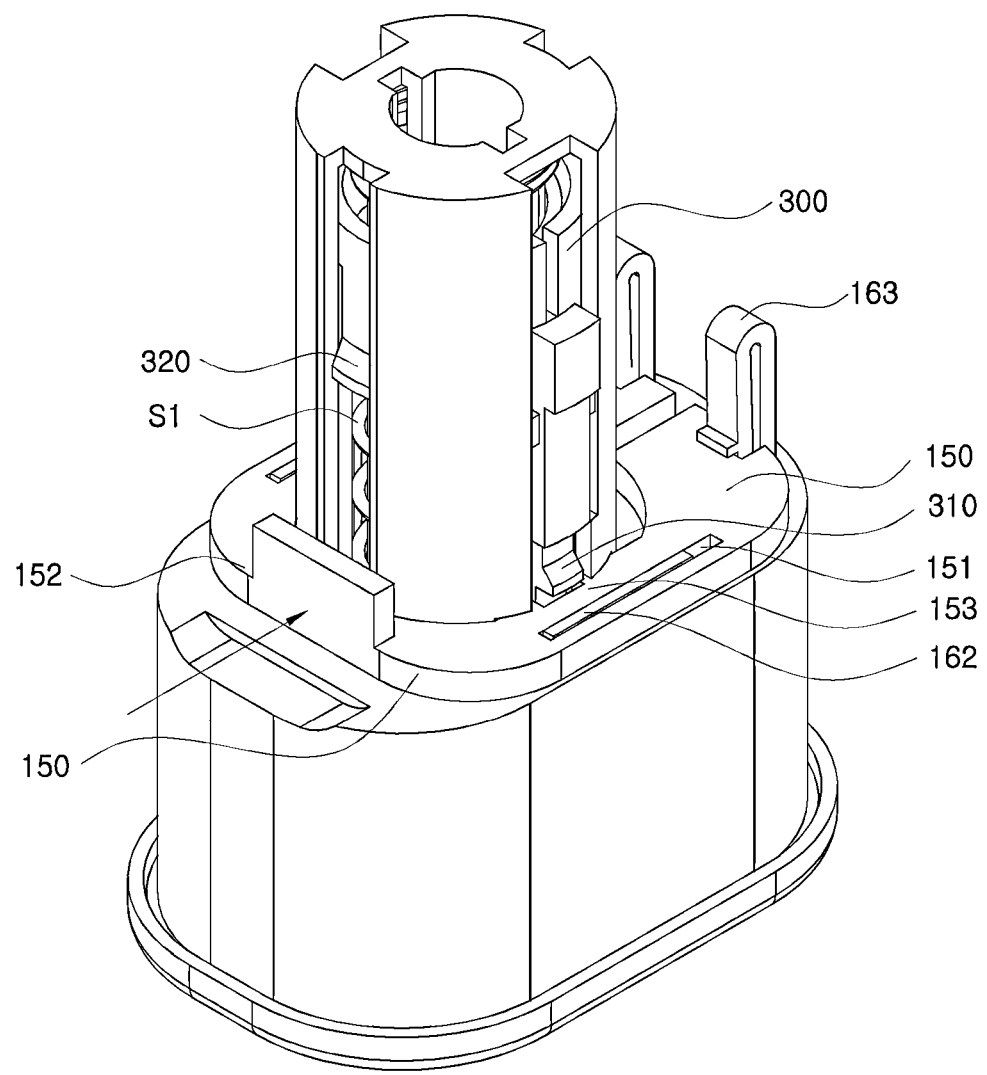

An interlock hook (310) is formed at the plunger body (300) to interlock with the shooting plate (150) as illustrated in FIGS. 12 and 13, the hanging protrusion part (153) interlockable with the interlock hook (310) of the plunger body (300) is formed at one side of the shooting plate (150), and the hanging protrusion part (153) may be configured to be released from the state interlocking with the interlock hook (310) as the shooting plate (150) is slidingly moved.

At the inner case (102), the guide rail (162) is formed to protrude to guide the slide movement path of the shooting plate (150), and the guide slot (151) is formed at the shooting plate (150) to insertedly guide the guide rail (162). And, an elastic structure (163) elastically supporting the shooting plate (150) in a direction opposite to a slide movement direction by the operation of the pressure button (110) is installed at the inner case (102). Accordingly, the shooting plate (150) is elastically supported by the pressure button (110) by the elastic force of the elastic structure (163), and therefore unless the pressure button (110) is manipulated for pressurization, the interlocking status of the plunger body (300) with the interlock hook (310) can be stably maintained.

Figure 15:
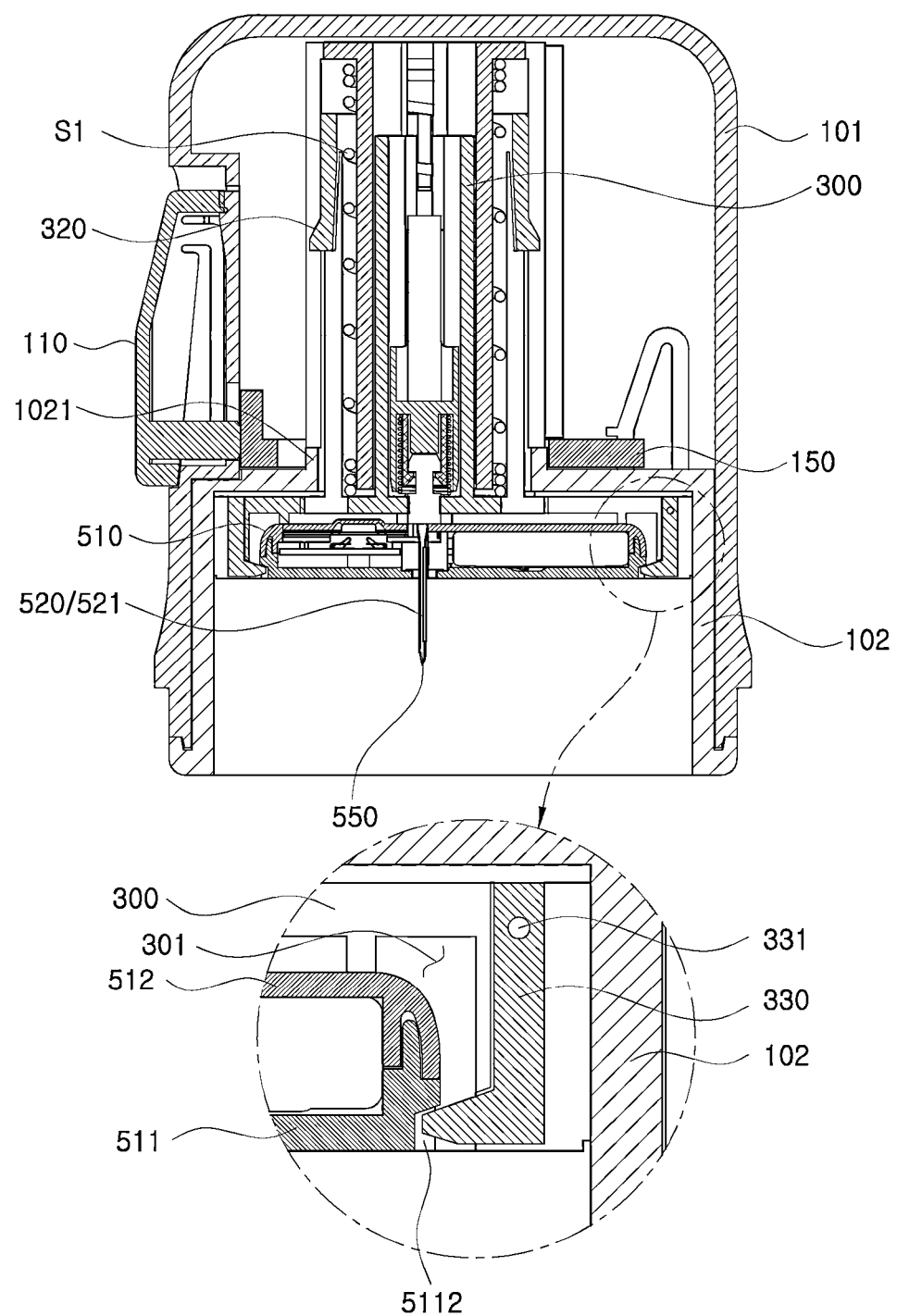
FIGS. 15 and 16 are views illustrating separation structures of an applicator and a body attachable unit according to an embodiment of the present disclosure.
Figure 16:
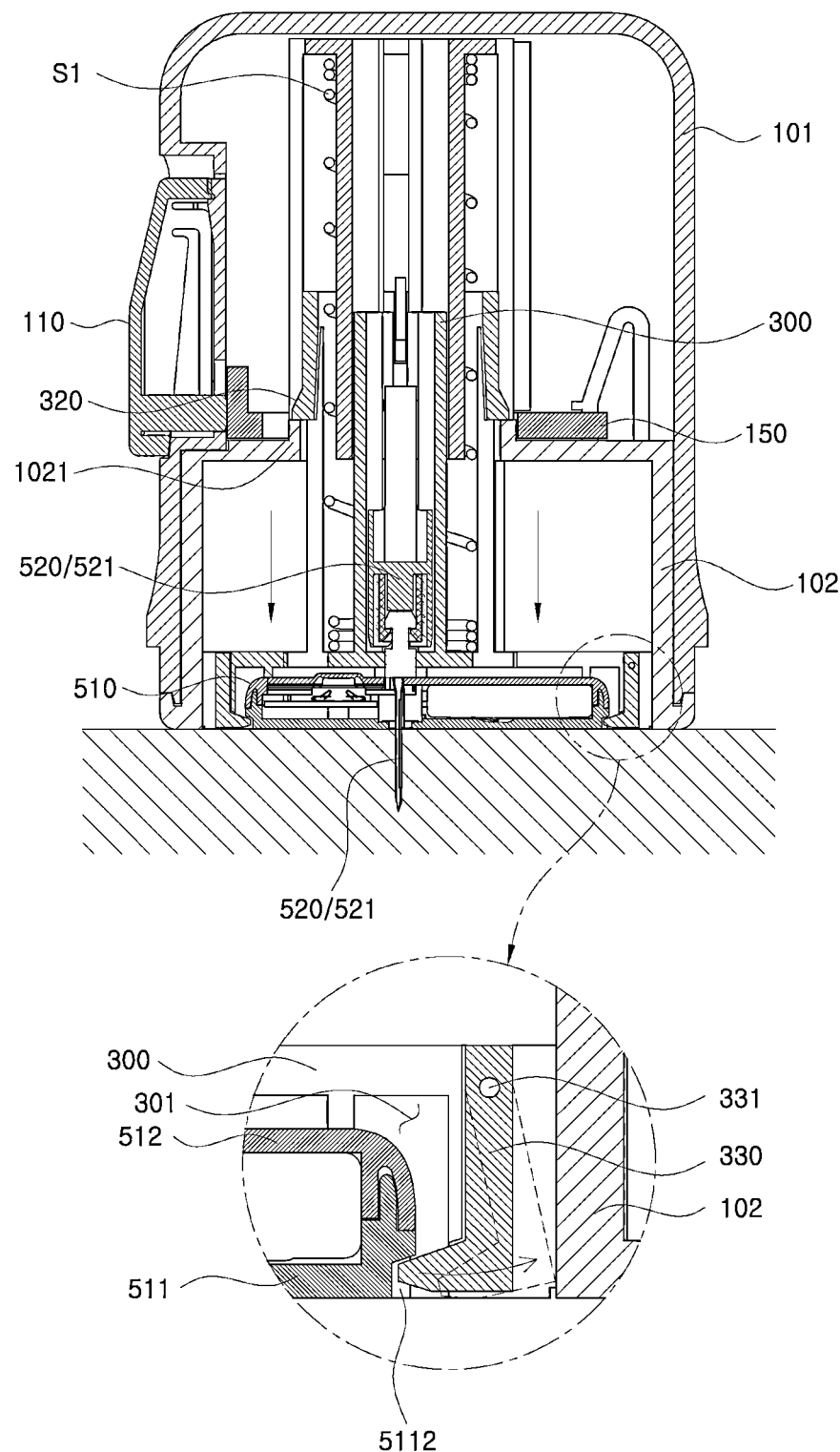

According to such a structure, when the user operates to pressurize the pressure button (110), the shooting plate (150) is slidingly moved, and this may result in releasing the interlocked state of the plunger body (300) and the shooting plate (150) and the plunger body (300) is outwardly discharged from the first location to the second location as shown in FIGS. 15 and 16.

A stopper protrusion (320) may be formed at the plunger body (300) to limit a range movable to the second location, and as the plunger body (300) is moved to the second location, the stopper protrusion (320) can limit the movement of the plunger body (300) by a way of being interlocked with one side of the inner case (102). Accordingly, the plunger body (300) can be moved up to the second location by the stopper protrusion (320), and the plunger body (300) cannot be outwardly discharged from the main case (100) over that range. In this embodiment, at the inner case (102), the plunger body (300) is interlocked with the stopper protrusion (320) in a state that the plunger body (300) is moved to the second location and a stopper fixing unit (1021) may be formed to limit the movement of the stopper protrusion (320).

Additionally, a sensor receiving unit (301) is formed at one end portion of the plunger body (300) so that the body attachable unit (20) is insertedly received, and the body attachable unit (20) is insertedly received by the sensor receiving unit (301) and linearly move together with the plunger body (300) from the first location to the second location. As the plunger body (300) and the body attachable unit (20) are linearly moved to the second location, the sensor probe (512) and the needle unit (550) of the body attachable unit (20) are inserted into the human body.

In this embodiment, a sensor fixing hook (330) fixedly coupling the body attachable unit (20) by being interlockedly coupled with the body attachable unit (20) inserted to the sensor receiving unit (301) is installed at an edge of the sensor receiving unit (301). An interlock coupling groove (5112) is formed at both end portions of the body attachable unit (20) to be interlocked with the sensor fixing hook (330) in a state that the body attachable unit (20) is inserted into the sensor receiving unit (301).

The sensor fixing hook (330) is coupled elastically rotatable around a rotary axis (331), in a state that the plunger body (300) is positioned at the first location as shown in FIG. 15 the sensor fixing hook (33) is elastically supported and pressurized in an inward direction so that the sensor fixing hook (330) is interlockedly coupled with the interlock coupling groove (5112) of the body attachable unit (20), and in a state that the plunger body (300) is positioned at the second location as illustrated in FIG. 16 the sensor fixing hook (330) is configured to be released from the interlock with the interlock coupling groove (5112) of the body attachable unit (20) in the operation of separating the applicator (10) from the body attachable unit (20). The operation of releasing the sensor fixing hook (330) from the interlock with the body attachable unit (20) can be performed in a way that the rotary shaft (331) twistingly and elastically rotates.

Although not illustrated, a hook guide unit (not shown) is formed on the inner surface of the inner case (102) and the hook guide unit pressurizes the sensor fixing hook (330) in an inward direction to be interlocked with the body attachable unit (20) and has a cross-sectional shape having a structure that the sensor fixing hook (330) is released from the pressurization in the state of the plunger body (300) moved to the second location. Therefore, the hook guide unit may have a structure with convex and concave surfaces on the inner surface of the inner case (102), the convex surface applies pressure to the sensor fixing hook (330) and the concave surface releases the sensor fixing hook (330) from the pressure application, and the concave is formed to release the sensor fixing hook (330) from the pressure application in a state that the sensor fixing hook (330) is moved together with the plunger body (300) to the second location.

Meanwhile, because the embodiment of the present disclosure is manufactured in a state that the body attachable unit (20) is inserted in the applicator (10), the reuse of the body attachable unit (20) by inserting again another body attachable unit (20) to the applicator (10) may be prevented as described above.

For this purpose, the main case (100) includes return prevention means for preventing the plunger body (300) returning to the first location after the plunger body (300) is moved to the second location.

Figure 17:
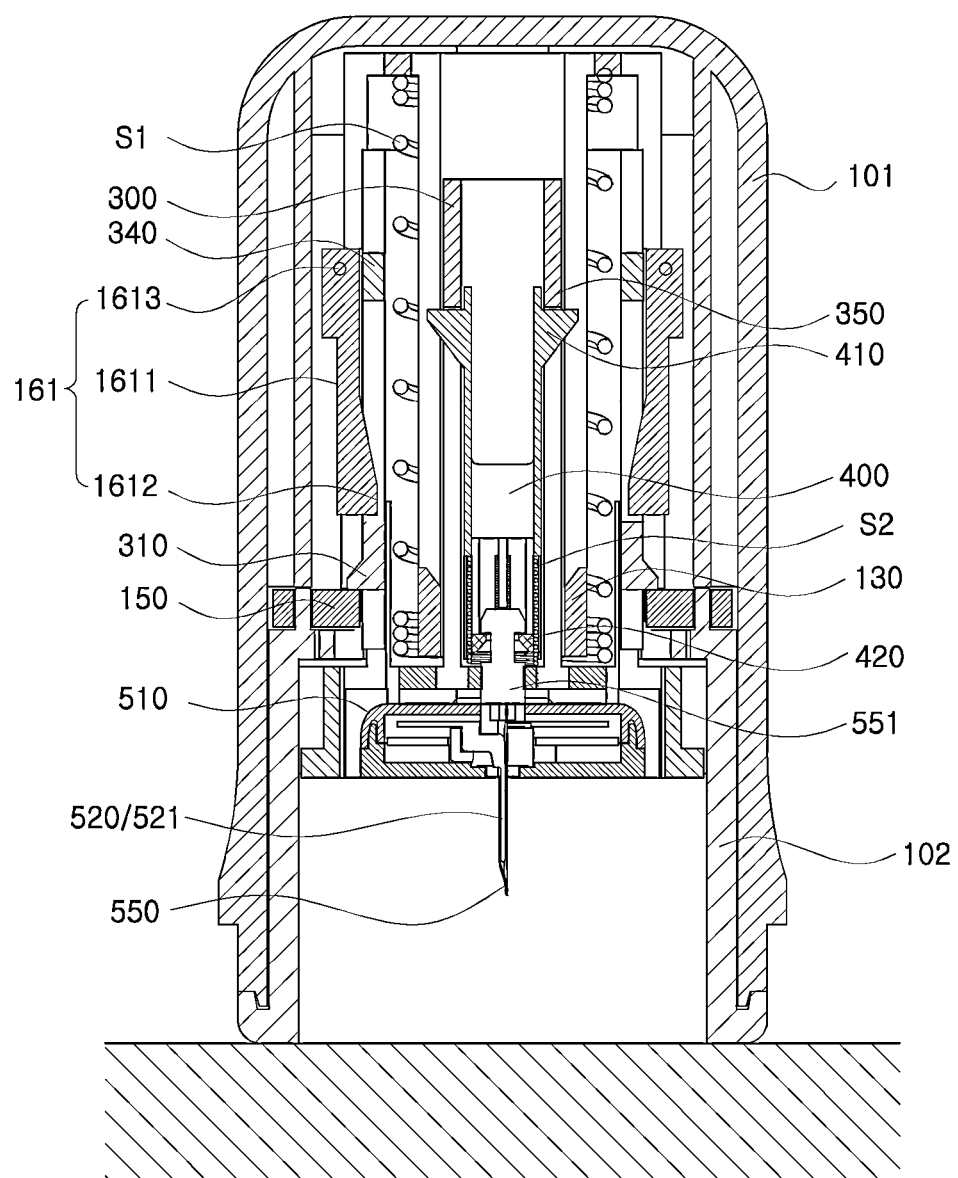
FIGS. 17 to 19 are views illustrating structures for preventing reuse of an applicator according to an embodiment of the present disclosure.
Figure 18:
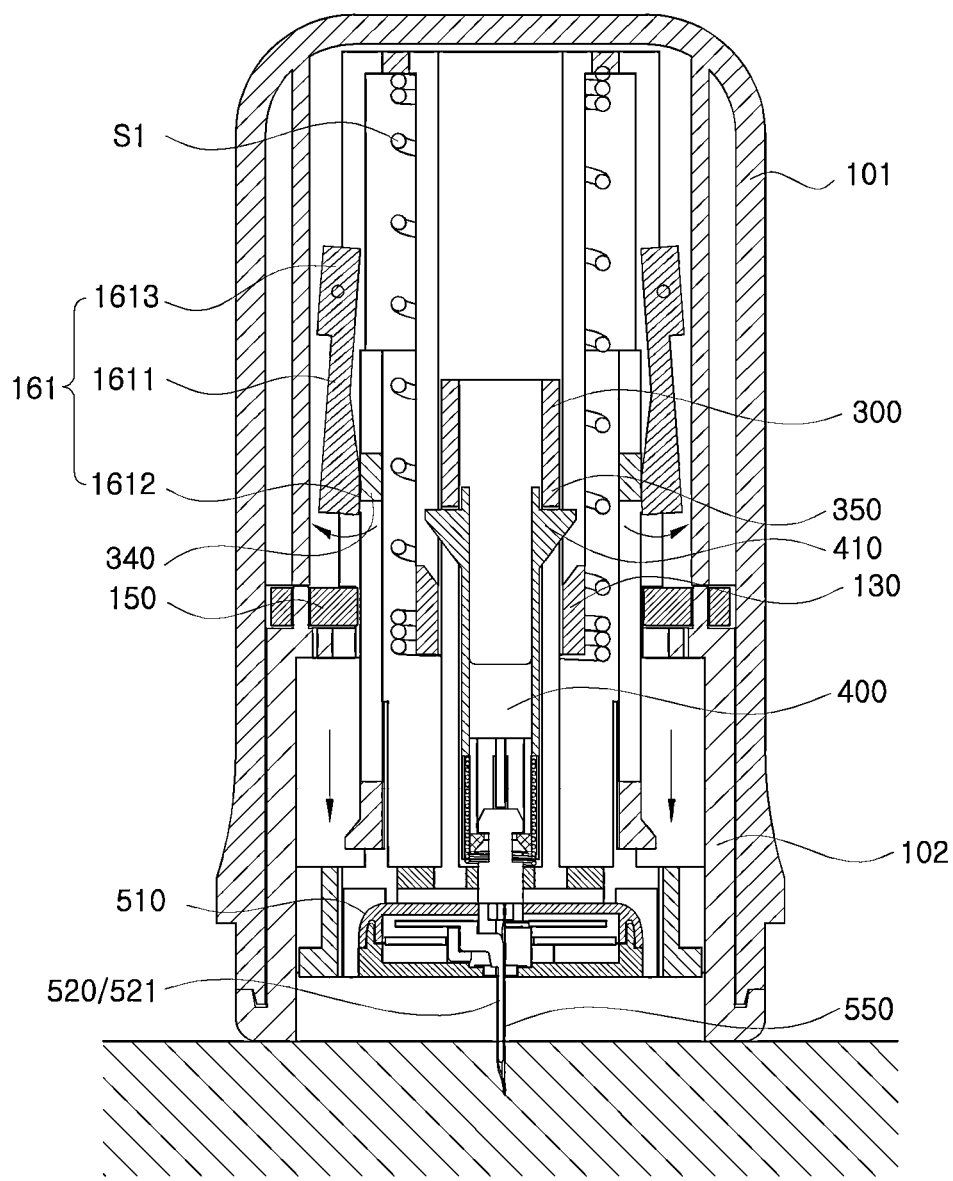
Figure 19:
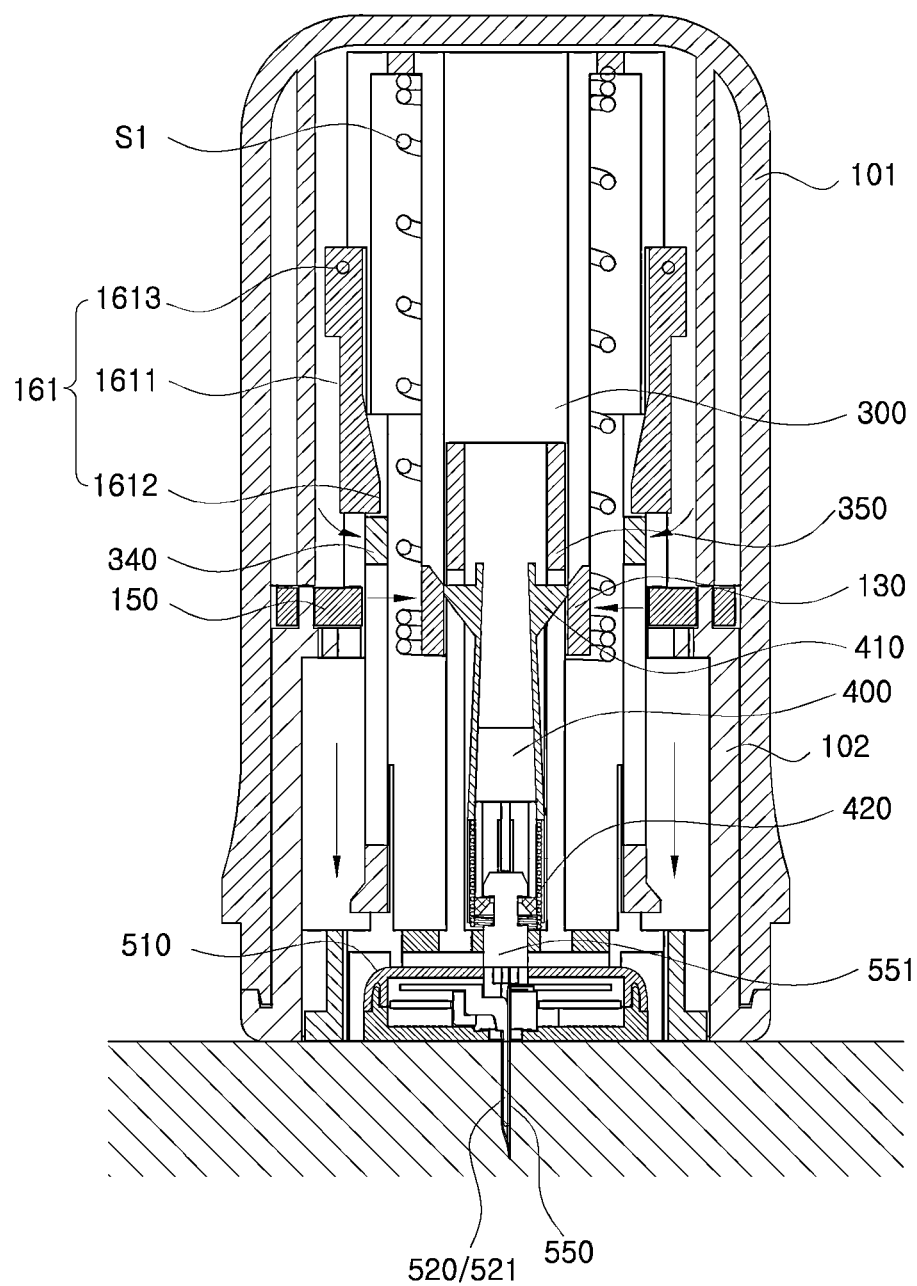

As illustrated in FIGS. 17 to 19, the return prevention means may be configured to comprise a interlocking body (340) formed on one side of the plunger body (300), and a return prevention hook (161) formed at the inner case (102) and configured to prevent the returning movement of the plunger body (300) by being interlockedly coupled with the interlocking body (340) of the plunger body (300) when the downward movement of the plunger body (300) from the first location to the second location is completed.

The return prevention hook (161) is configured to be interlocked with the interlocking body (340) by elastic restoring force in the operation of be interlocked with the interlocking body (340). Specifically, the return prevention hook (161) may be configured to have a structure comprising a rotatable body (1611) elastically rotatably coupled around a rotary shaft (1613) and at one side of the inner case (102), and a hook body (1612) slantly protruding from the inner side surface of the rotatable body (1611) in a downward and inward direction. In this embodiment, the rotary axis (1613) is configured to elastically support the rotatable body (1611) in a inward and protruding direction of the hook body (1612) by applying elastic force according to a material character of elastic material.

By this return prevention hook (161), the returning movement of the plunger body (300) to the first location after the movement from the first location to the second location is completed is prevented, and therefore, the user's inserting and using another body attachable unit (20) again at the user's discretion may be prevented.

The state of the operation of the return prevention hook (161) will be described in detail, and if the plunger body (300) is moved to the second location by the operation of the pressure button (110) in a state that the plunger body (300) is positioned at the first location as shown in FIG. 17, the hook body (1612) is pressurized by the interlocking body (340) of the plunger body (200) during the movement of the plunger body (300) to the second location as illustrated in FIG. 18, and then the return prevention hook (161) is elastically rotated in a clockwise direction (an outward direction) around the rotary axis (1613). After that, if the movement of the plunger body (300) to the second location is completed as shown in FIG. 19, the return prevention hook (161) is returned by being elastically rotated around the rotary shaft (1613) in a count-clockwise direction (an inward direction). Likewise, as the return prevention hook (161) is elastically return-rotated, the lower portion of the return prevention hook (161) is interlocked with the upper portion of the interlocking body (340) of the plunger body (300), and therefore the returning movement of the plunger body (300) to the first location in a state interlocking with the return prevention hook (161) and the interlocking body (340) is prevented.

Meanwhile, the applicator (10) is configured to extract and remove the needle unit (550) of the body attachable unit (20) from the human body at a time of the completion of outward discharge movement of the body attachable unit (20) from the first location to the second location, and for this purpose, the applicator (10) may comprise a needle extracting means (N) configured to upwardly move the needle unit (550) and extract and remove the needle unit (550) from the human body at a time of the completion of the movement of the plunger body (300) from the first location to the second location.

The needle extracting means (N) may comprise a needle extracting body (400) coupled with the needle head (551) of the needle unit (550) and linearly move along the inner case (102) from the first location to the second location together with the plunger body (300) by being interlocked with the plunger body (300), and a needle extracting elastic spring (S2) applying elastic force to the needle extracting body (400) in a direction that the needle extracting body (400) upwardly moves toward the first location.

The needle extracting body (400) is interlockedly coupled to the plunger body (300), and for this purpose, a separate elastic hook (410) configured to be elastically transformable is provided at the needle discharge body (400), and the elastic hook (410) is elastically biased in a direction interlockedly coupled to the hook interlocking unit (350) of the plunger body (300). Accordingly, if the plunger body (300) is linearly moved from the first location to the second location according to the operation of the pressure button (110), the needle extracting body (400) is also linearly moved to the second location together with the plunger body (300).

In this embodiment, a needle extracting pressurizing unit (130) configured to pressurize the elastic hook (410) in an inward direction so that the elastic hook (410) is released from the interlock with the hook interlocking unit (350) of the plunger body (300) according to the movement of the needle extracting body (400) to the second location is included in the inner case (102).

Figure 20:
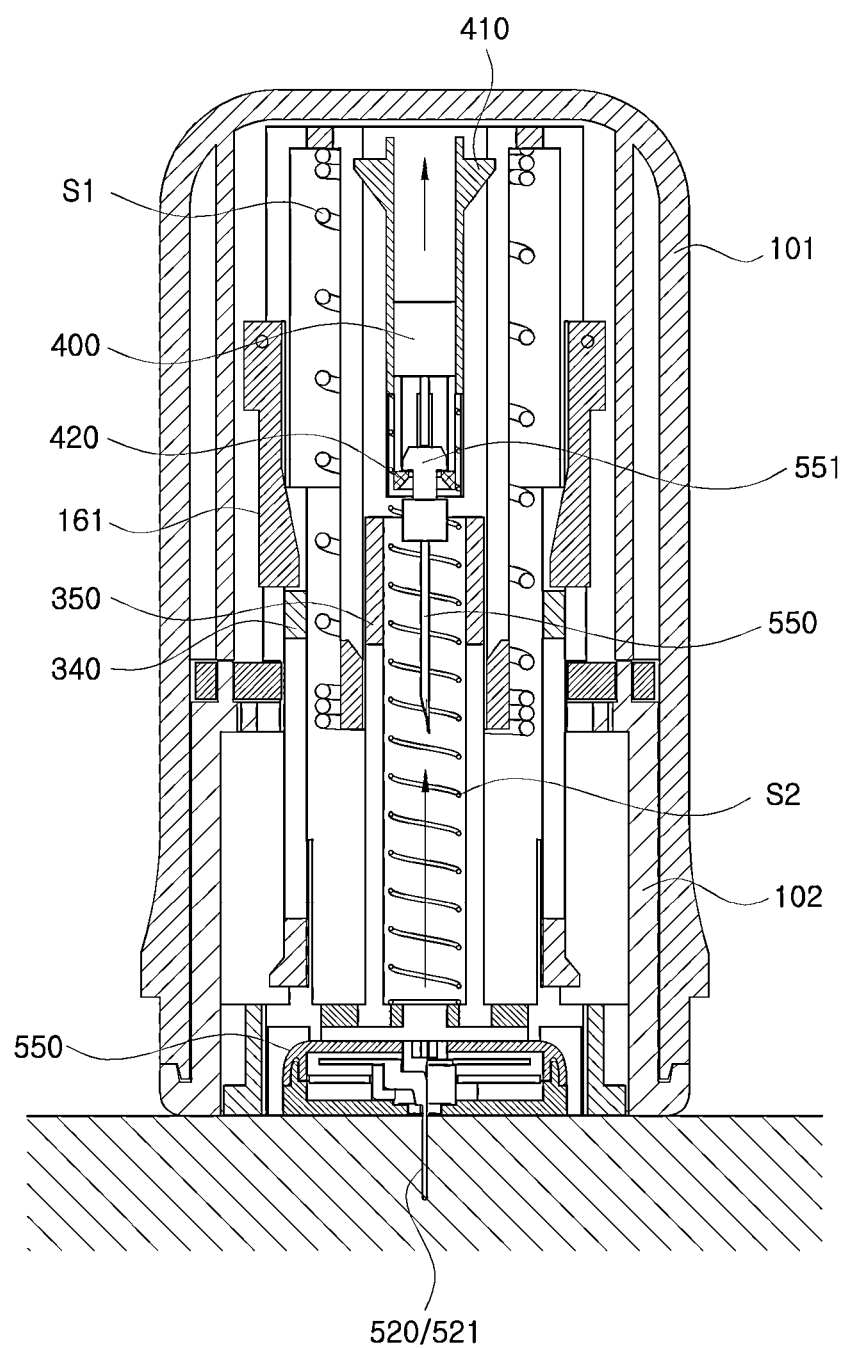
FIG. 20 is a view illustrating an operation structure of needle extracting means according to an embodiment of the present disclosure.

If the pressure is applied to the pressure button (110) according the structures described above, the needle extracting body (400) linearly moves from the first location to the second location together with the plunger body (300) as illustrated in FIG. 19, at the same time the elastic hook (410) of the needle extracting body (400) is pressurized by the needle extracting pressurizing unit (130) and is released from the state interlocked with the hook interlocking unit (350), and therefore the needle extracting body (400) is upwardly return-moved toward the first location by the elastic force of the needle extracting elastic spring (S2) as shown in FIG. 20.

In this embodiment, because the needle extracting body (400) is coupled with the needle head (551) of the needle unit (550) through an end of a needle head coupling unit (420), during the operation that the needle extracting body (400) is upwardly return-moved, the needle unit (550) is moved together and removed from the human body. The needle head coupling unit (420) is formed at the lower end portion of the needle extracting body (400) by a form of being interlockedly coupled to the coupling groove (552) formed at the needle head (551).

Meanwhile, according to the movement of the plunger body (300) to the second location by the elastic force of the plunger elastic spring (S1) the sensor probe (521) and the needle unit (550) of the body attachable unit (20) is inserted into the human body, but the needle unit (550) may be slightly retracted in a direction opposite to a human body insertion direction by reaction force generated by insertion resistance during the process of inserting the needle unit (550) to the human body. In this case, because the sensor probe (521) is not inserted into the human body to a proper depth, the retraction of the needle unit (550) needs to be prevented. For this, a needle supporting block may be coupled to the needle attachable body (400), and the needle supporting block is configured to downwardly support an upper end of the needle unit (550) so that the needle unit (550) cannot be upwardly moved with respect to the needle extracting body (400).

Next, use states of the assembly of the sensor applicator described above will be described with respect to FIGS. 21 to 25.

FIGS. 21 to 25 are views illustrating use states of a continuous blood glucose measurement apparatus according to operation order step by step according to an embodiment of the present disclosure.

Figure 21:
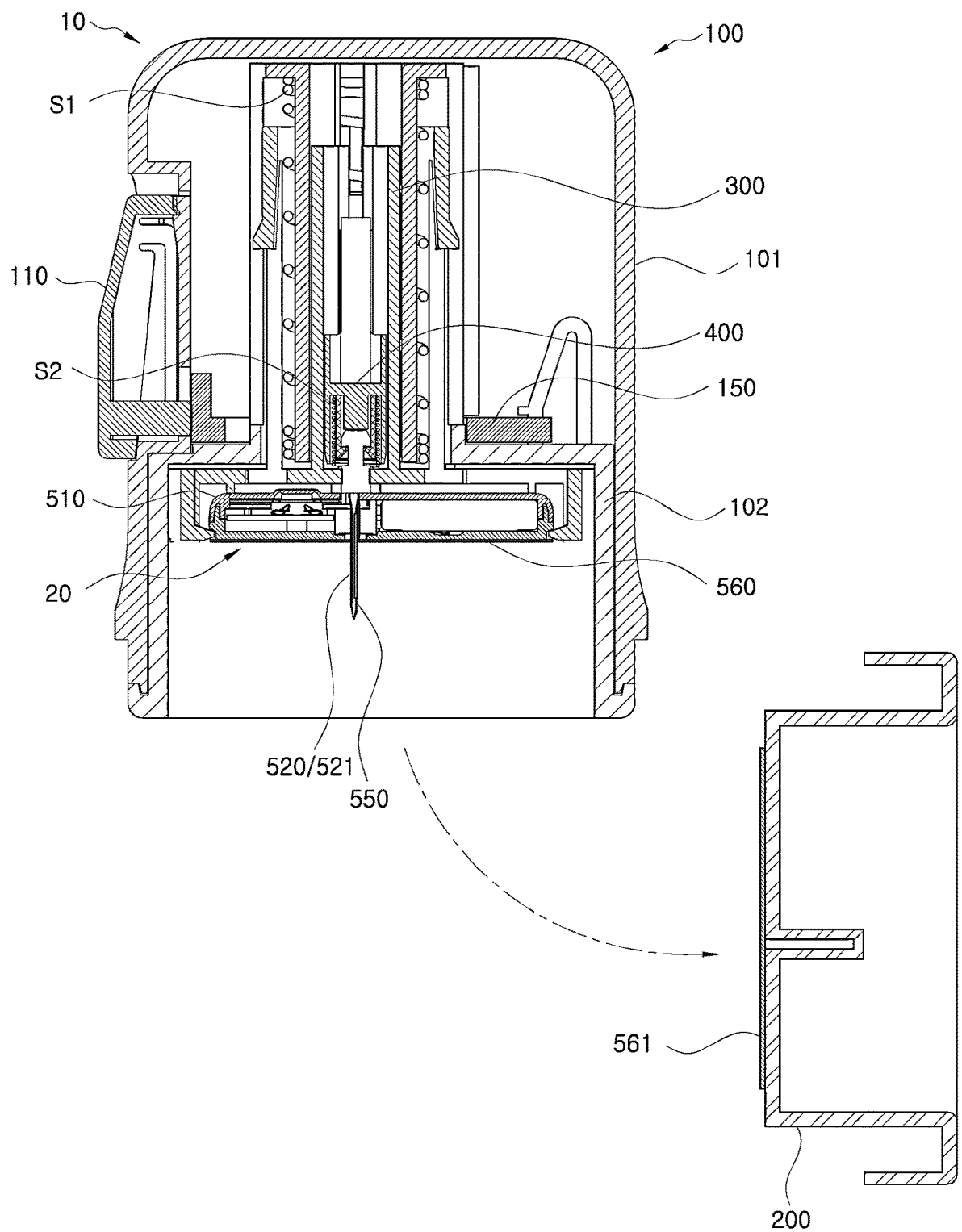
FIGS. 21 to 25 are views illustrating use states of a continuous blood glucose measurement apparatus according to operation order step by step according to an embodiment of the present disclosure.

First, as illustrated in FIG. 21, the protection cap (200) of the applicator (10) is separated. In the operation of separating the protection cap (200), the release paper (561) of the adhesive tape (560) of the body attachable unit (20) is separated together with the protection cap (200) and removed from the adhesive tape (560). After that, the sensor applicator assembly is located on a position of the human body to attach the body attachable unit (20), and in this state, after changing a mode of the pressure button (110) from the safe mode to the pressurization standby mode, the pressure button (110) is operated to be pressurized.

Figure 22:
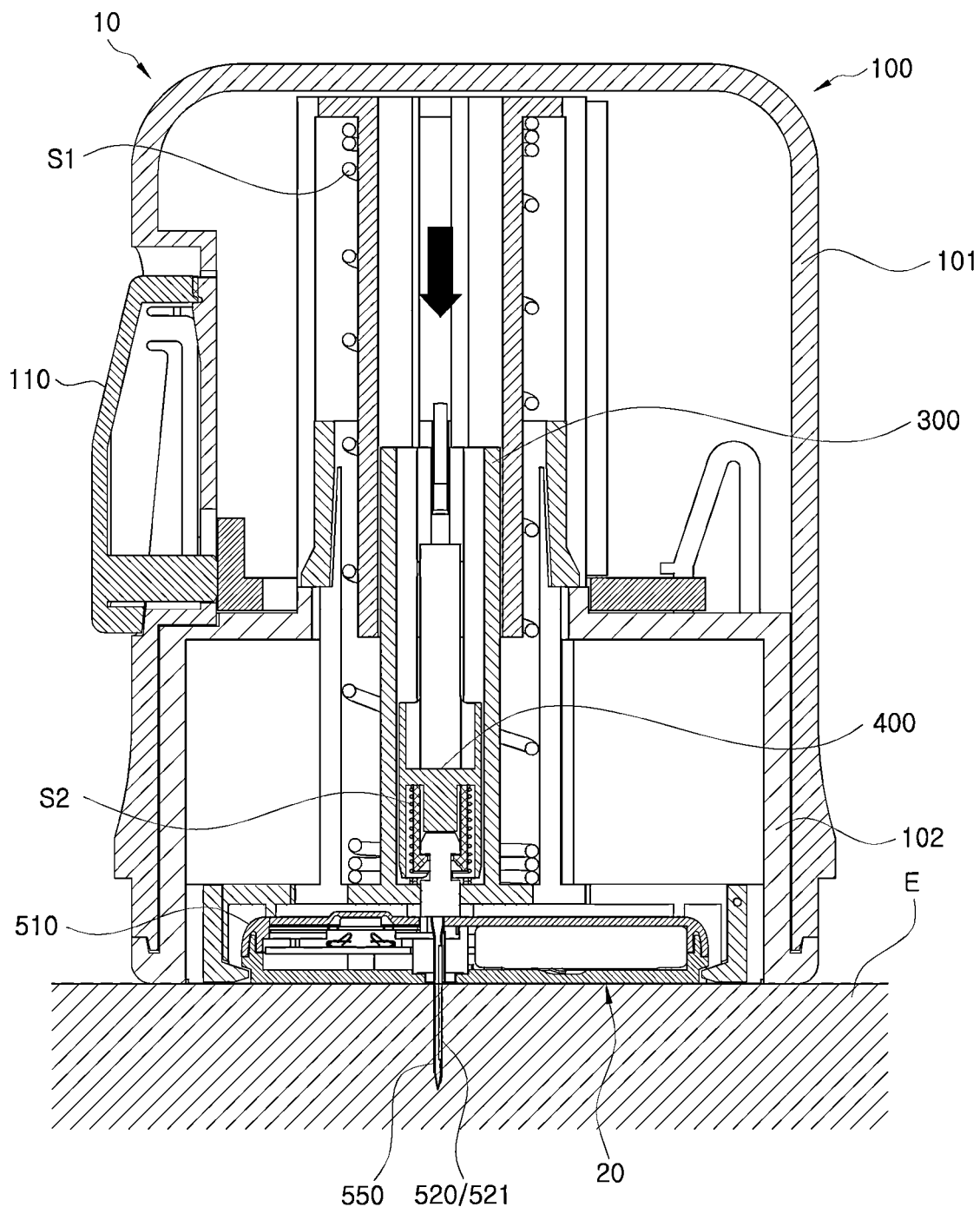
Figure 23:
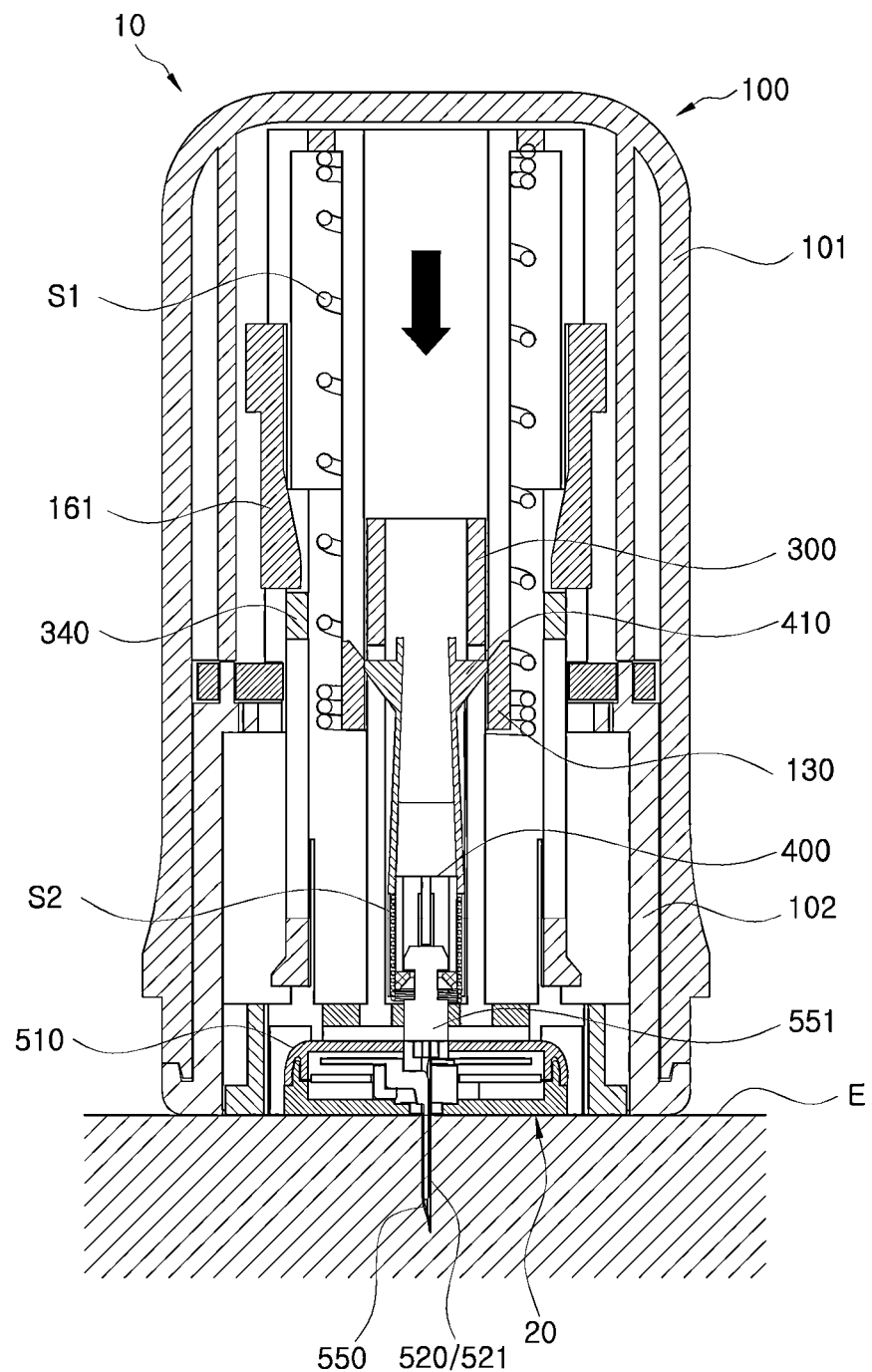

If the pressurizing operation is performed to the pressure button (110), the state interlocking with the plunger body (300) is released by the movement of the shooting plate (150), therefore the plunger body (300) is downwardly moved in a direction outwardly discharged by the plunger elastic spring (S1) as illustrated in FIGS. 22 and 23, and in this process, the needle unit (550) and the sensor probe (521) of the body attachable unit (20) is inserted into the human body (E). In this time, the body attachable unit (20) is adhered to a surface of the human body (E) by the bottom surface of the adhesive tape (560). Likewise, if the plunger body (300) is moved in an outwardly discharged direction, the plunger body (300) is interlocked by the return prevention hook (161) of the inner case (102) and therefore the plunger body (300) cannot upwardly move again as illustrated in FIG. 23. Accordingly, an applicator (10) which is already used cannot be reused again.

If the plunger body (300) is downwardly moved, the sensor fixing hook (330) of the sensor receiving unit (301) can be received from a state interlockedly coupled with the body attachable unit (20) as illustrated in FIG. 23. Additionally, the elastic hook (410) of the needle extracting body (400) is pressurized in an inward direction by the needle extracting pressurizing unit (130) of the inner case (102) and the state interlocked with the plunger body (300) is released.

Figure 24:
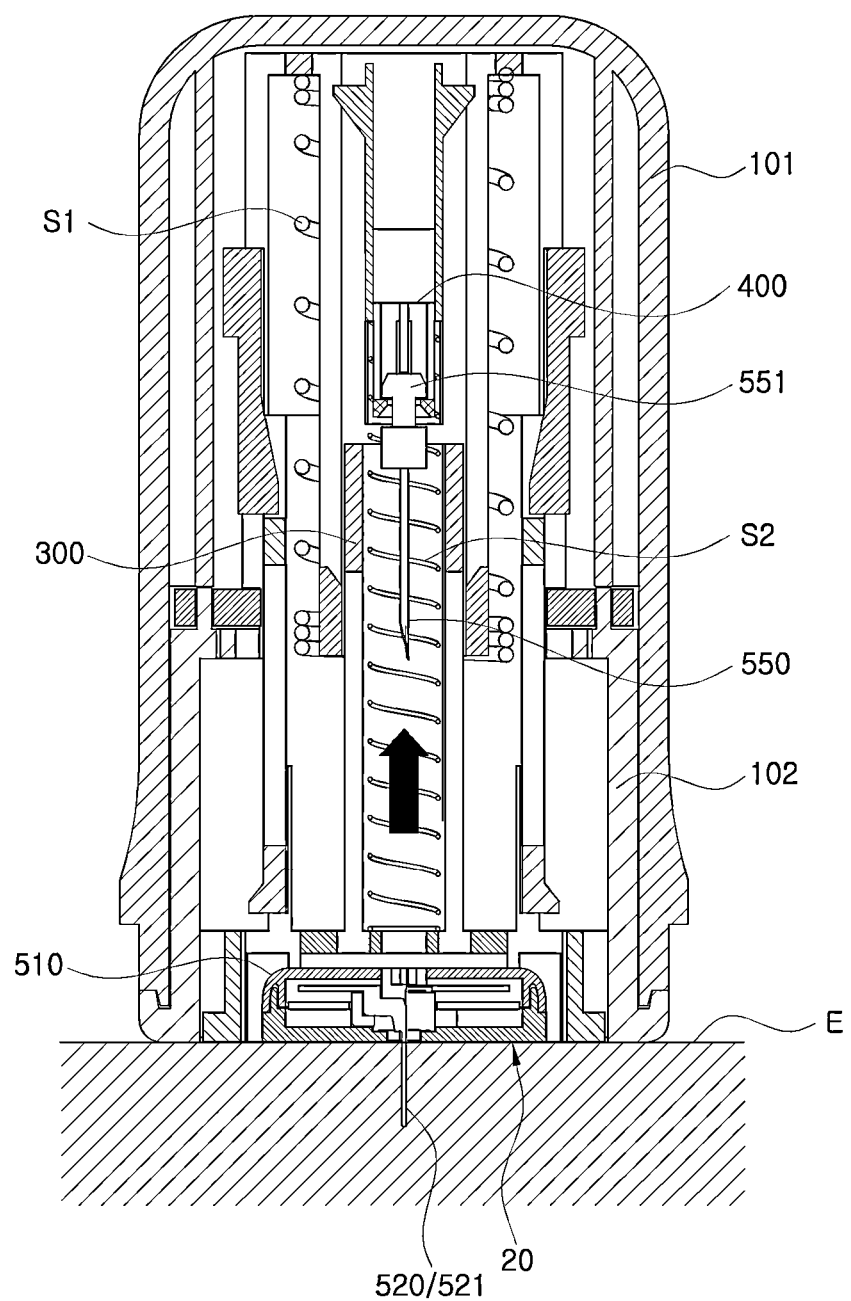

Accordingly, if the plunger body (300) is downwardly moved, at the same time the needle extracting body (400) is upwardly return-moved by the needle extracting elastic spring (S2) as illustrated in FIG. 24. In this time, because the needle unit (550) is upwardly moved together with the needle extracting body (400), the needle unit (550) is extracted and removed from the human body (E).

Figure 25:
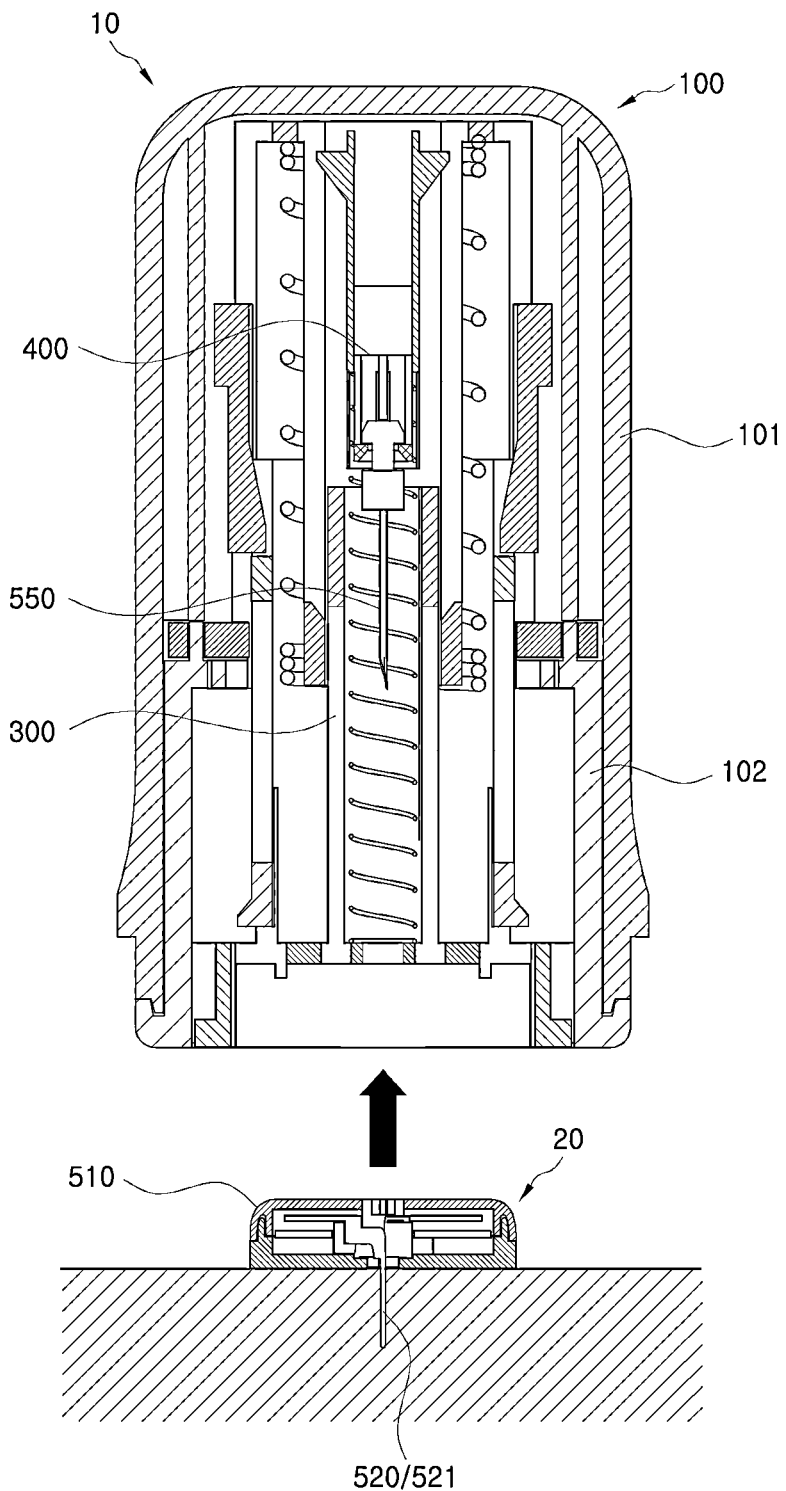

In this state, because the interlock between the sensor fixing hook (330) and the body attachable unit (20) is releasable as described above, the applicator (10) can be upwardly separated and removed as shown in FIG. 25, and if the applicator (10) is separated and removed in this way, only the body attachable unit remains in the state attached to the human body (E).

After that, the sensor unit (520) and the wireless communication chip (540) of the body attachable unit (20) can initiate operation by the operation of a pressurizing operation module (570) of the body attachable unit (20) and so on, and therefore the measurement result of the blood glucose by the body attachable unit (20) can be transmitted to a separate external terminal. According to an embodiment of the present disclosure, because both of the sensor unit (520) and the wireless communication chip (540) are installed to the body attachable unit (20), no additional work for connecting and coupling a separate transmitter is needed.

Next, details of the body attachable unit (20) will be described according to an embodiment of the present disclosure.

Figure 26:
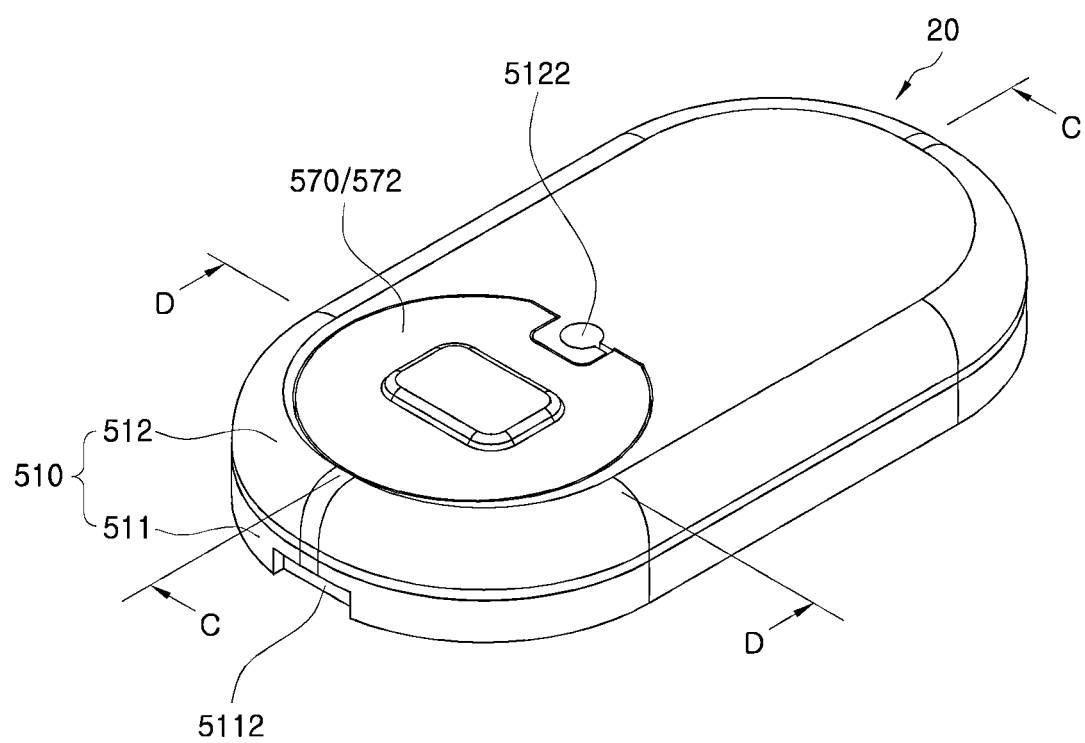
FIG. 26 is a perspective view conceptually illustrating an outer structure of a body attachable unit attached to a human body according to an embodiment of the present disclosure.
Figure 27:
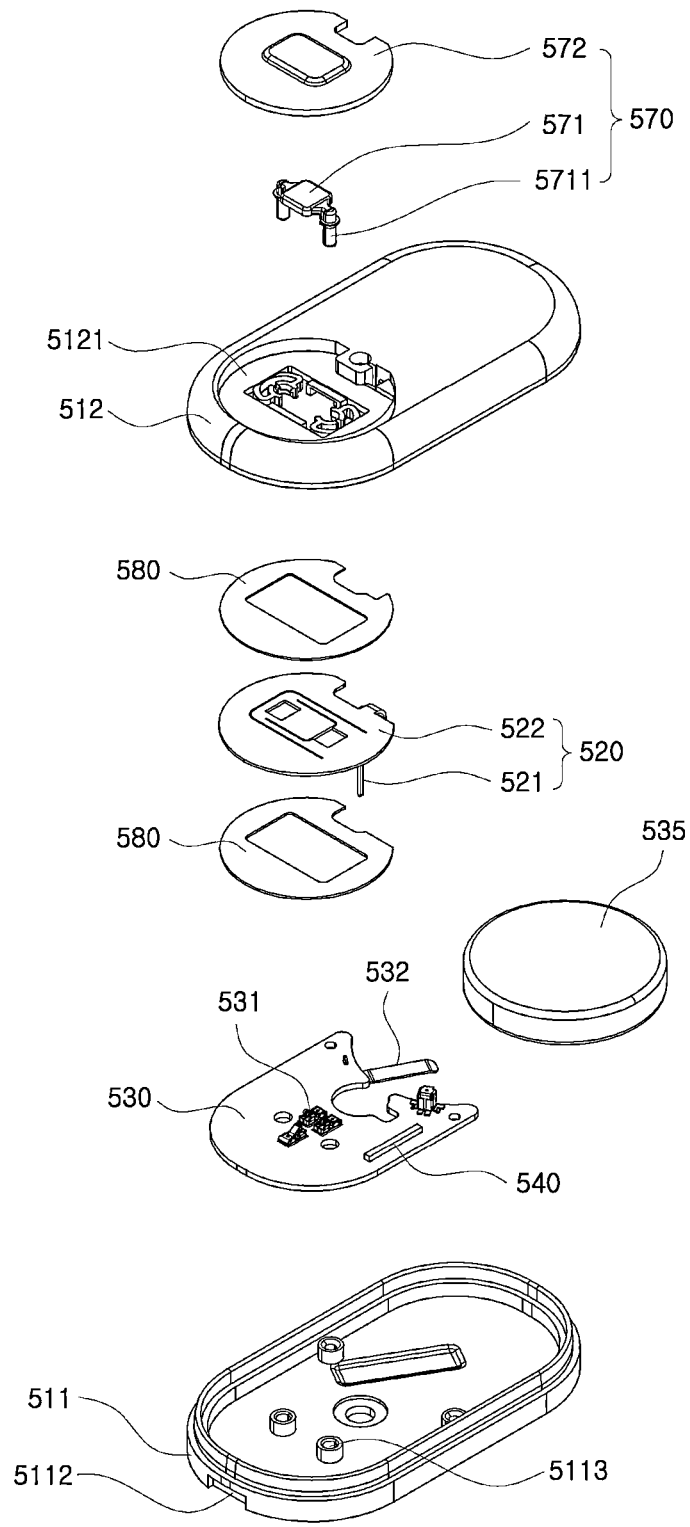
FIG. 27 is an exploded perspective view conceptually illustrating components of a body attachable unit.
Figure 28:
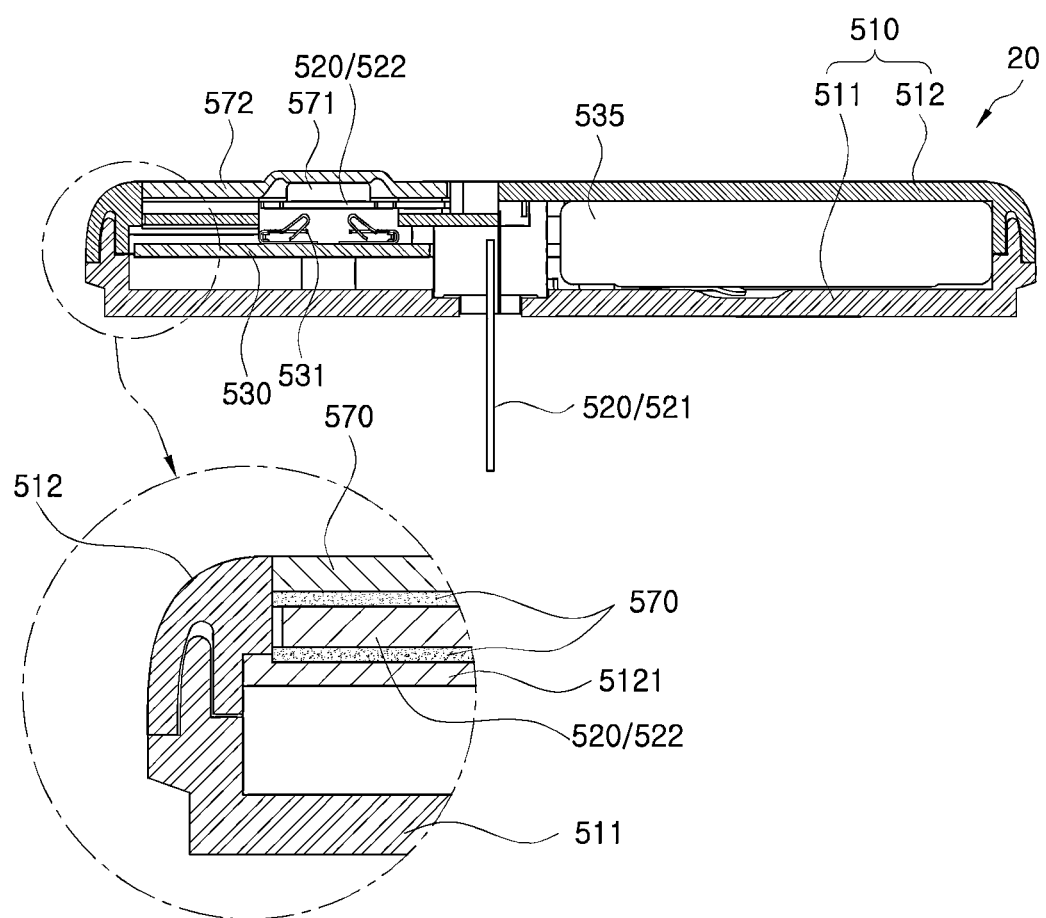
FIG. 28 is a cross-sectional view taken along line "C-C" of FIG. 26.
Figure 29:
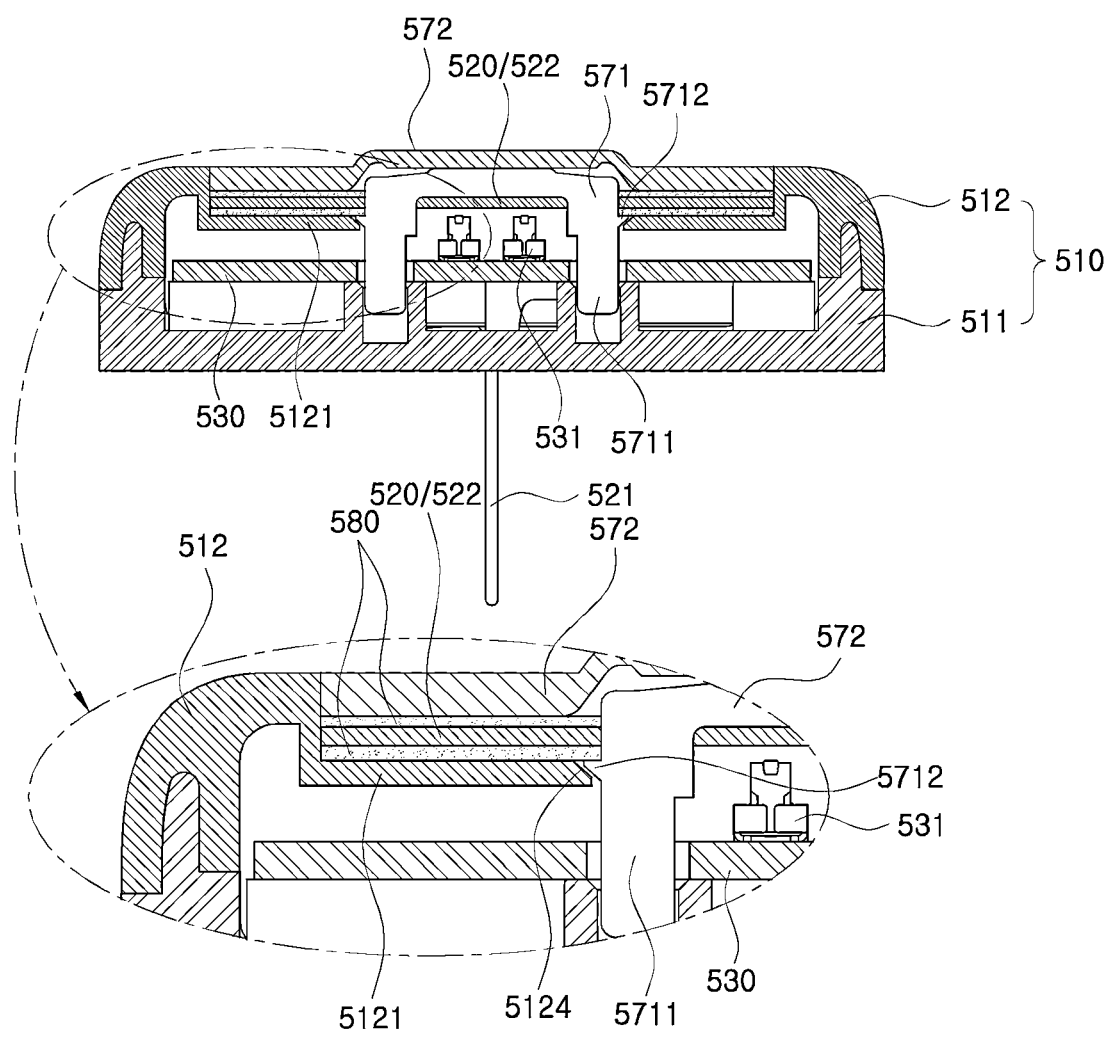
FIG. 29 is a cross-sectional view taken along line "D-D" of FIG. 26.
Figure 30:
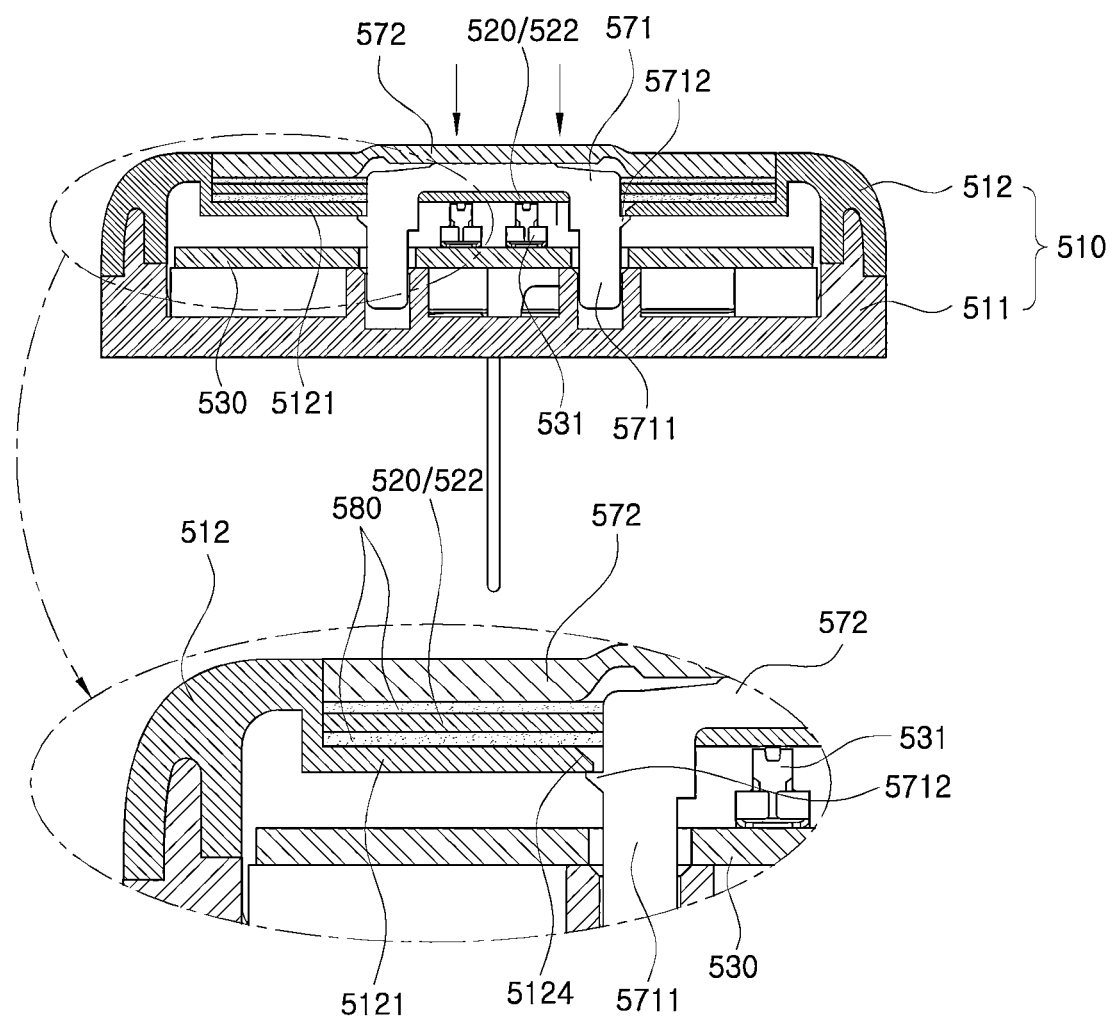
FIG. 30 is a conceptual view illustrating a operation state of a pressurizing operation module according to an embodiment of the present disclosure.

FIG. 26 is a perspective view conceptually illustrating an outer structure of a body attachable unit attached to a human body according to an embodiment of the present disclosure, FIG. 27 is an exploded perspective view conceptually illustrating components of a body attachable unit, FIG. 28 is a cross-sectional view taken along line "C-C" of FIG. 26, FIG. 29 is a cross-sectional view taken along line "D-D" of FIG. 26, and FIG. 30 is a conceptual view illustrating a operation state of a pressurizing operation module according to an embodiment of the present disclosure.

The body attachable unit (20) according to an embodiment of the present disclosure is configured to comprise the housing (510) to which the adhesive tape (560) is attached so that a bottom side of the housing (510) can be attached to skin, the sensor unit (520) disposed inside the housing (510) so that one end portion of the sensor unit (520) externally protrudes from the bottom side of the housing (10) and is inserted into the human body when the housing (510) is attached to the skin, and a PCB board (530) arranged inside the housing 510).

One end portion of the sensor unit (520) is formed to be inserted into the human body and the other end portion of the sensor unit (520) is formed to contact the PCT board (530), a sensor body unit (522) is formed at the other end of the sensor unit (520) to be contacted with an electrical contact point of the PCB board (530), and a sensor probe unit (521) is formed at the one end portion and the sensor probe unit (521) is formed to extend in the form of being bent from one side of the sensor body unit (522) and outwardly protrudes from the housing (510) and is inserted into the human body. The sensor body unit (522) is formed to have a structure with a relatively large area, and the sensor probe unit (521) is formed to have a relatively narrow and long structure.

The housing (510) may be formed to be divided into a upper housing (512) and a lower housing (511) to form an inner accommodating space, a sensor supporting unit (5121) supporting the sensor body unit (522) to be spaced apart from the electrical contact point (531) of the PCB board (530) at a certain distance is formed inside the housing (510), and a sensor guide unit (not shown) configured to support and guide a certain section of the sensor probe unit (521) is also formed inside the housing (510). Additionally, a board supporting unit (5113) for fixedly supporting the PCT board (530) at a certain location may be also formed inside the housing (510).

The electrical contact point (531) is formed at the PCB board (530) to be electrically connected with the sensor unit (520), and the wireless communication chip (540) is installed to the PCB board (530) to transmit the glucose measurement result measured by the sensor unit (520) to an external terminal. According to an embodiment of the present disclosure, by installing the wireless communication chip (540) at the inside of the body attachable unit (20), the communication with the external terminal can be easily performed without a work connecting a separate transmitter.

Further, a battery (535) configured to supply power to the PCB board (530) is installed at the inside of the housing (510), and the battery (535) is not installed at one side of the PCB board (530) but disposed at an area independent from the PCB board (530). Accordingly, the PCB board (530) and the battery (535) are independently arranged so that any area of the PCB board (530) and the battery (535) projecting into the bottom surface of the housing (530) cannot overlap each other. By arranging the PCB board (530) and the battery (535) to areas independent to each other, respectively, the thickness of the body attachable unit (20) may be reduced and the size of the body attachable unit (20) may be more minimized. In this embodiment, at the PCT board (530), a separate contact terminal (532) may be formed to extend to the battery (535) to be electrically contacted and connected to the battery (535).

The body attachable unit (20) according to an embodiment of the present disclosure is formed so that the other end portion of the sensor unit (520), i.e., the sensor body unit (522), is contacted to the electrical contact point (531) of the PCB board (530) by the manipulation or operation of the user, and according to this electrical contact, the operation of the body attachable unit (20) may be initiated. Accordingly, the embodiment of the present embodiment is configured to perform the power supply as well as the initiation of the operation of the sensor unit (520), the wireless communication chip (540) and other components by the electrical connection of the sensor unit (520) and the PCB board (530) by the manipulation of the user.

The housing (510) may have a separate pressurizing operation module (570) activated by the operation of the user to connect the other end portion of the sensor unit (520) and the electrical contact point (531) of the PCB board (530) by the operation of the user.

The pressurizing operation module (570) is movably connected to the housing (510) and may comprise a movable pressurizing body (571) configured to be movable in a pressurizing direction by the pressure applied by the user, and according to the movement of the movable pressurizing body (571) at least a partial area of the other end portion of the sensor unit (520) is transformed by the pressure of the movable pressurizing body (571) and contacted to the electrical contact point (531) of the PCB board (530).

Additionally, the pressurizing operation module (570) may further comprises a button cover (572) having flexible material and a structure covering an outer surface of the movable pressurizing body (571) and coupled to the housing (510) so that the button cover (572) can be exposed to the outside of the body attachable unit (20) in order to be capable of the pressurizing operation by the user, and the coupling portion between the button cover (572) and the housing (510) may be processed to be sealed.

In this embodiment, the seal processing means at the coupling portion between the button cover (572) and the housing (510) may be configured to use a double-side tape (580). For example, one side of the double-side tape (580) is adhered to the other portion of the sensor unit (520), such as one side of the sensor body unit (522), along its circumferential edge, the other side of the double-side tape (580) is adhered to the inner-side surface of the button cover (572) along its circumferential edge, and this double-side tape (580) can seal the circumferential edge of the button cover (572). In this embodiment, the double-side tape (580) may be adhered to the other side of the sensor body unit (522) along the circumferential edge as well, and by this, the sensor body unit (522) may be adhered and fixed to the sensor supporting unit (5121) along the circumferential edge of the sensor body unit (522) by using the double-side tape (580).

In a state that the circumferential edge of the sensor body (522) is adhered and fixed to the sensor supporting unit (5121) by the double-side tape (580), the center section of the sensor body unit (522) is transformed by the pressure of the movable pressurizing body (571) and may contact the electrical contact point of the PCB board (530) as illustrated in FIG. 30. Although the movable pressurizing body (571) is moved in the pressurized direction, because the button cover (572) is made of flexible material and the circumferential edge portion of the button cover (572) is adhered to the housing (510) by the double-side tape (580), only the center portion of the button cover (572) is transformed in the pressurized direction and the circumferential edge portion of the button cover (572) is adheredly fixed and remains the sealed state.

Meanwhile, it is preferred that after the sensor body unit (522) is contacted to the electrical contact point (531) of the PCB board (530) by the operation of the user the contact status can be stably maintained for stable measurement of blood glucose, and for this, the movable pressurizing body (571) is formed to be fixedly positioned in a state that the movable pressurizing body (571) is moved in a pressurized direction by the urging force.

Figure 31:
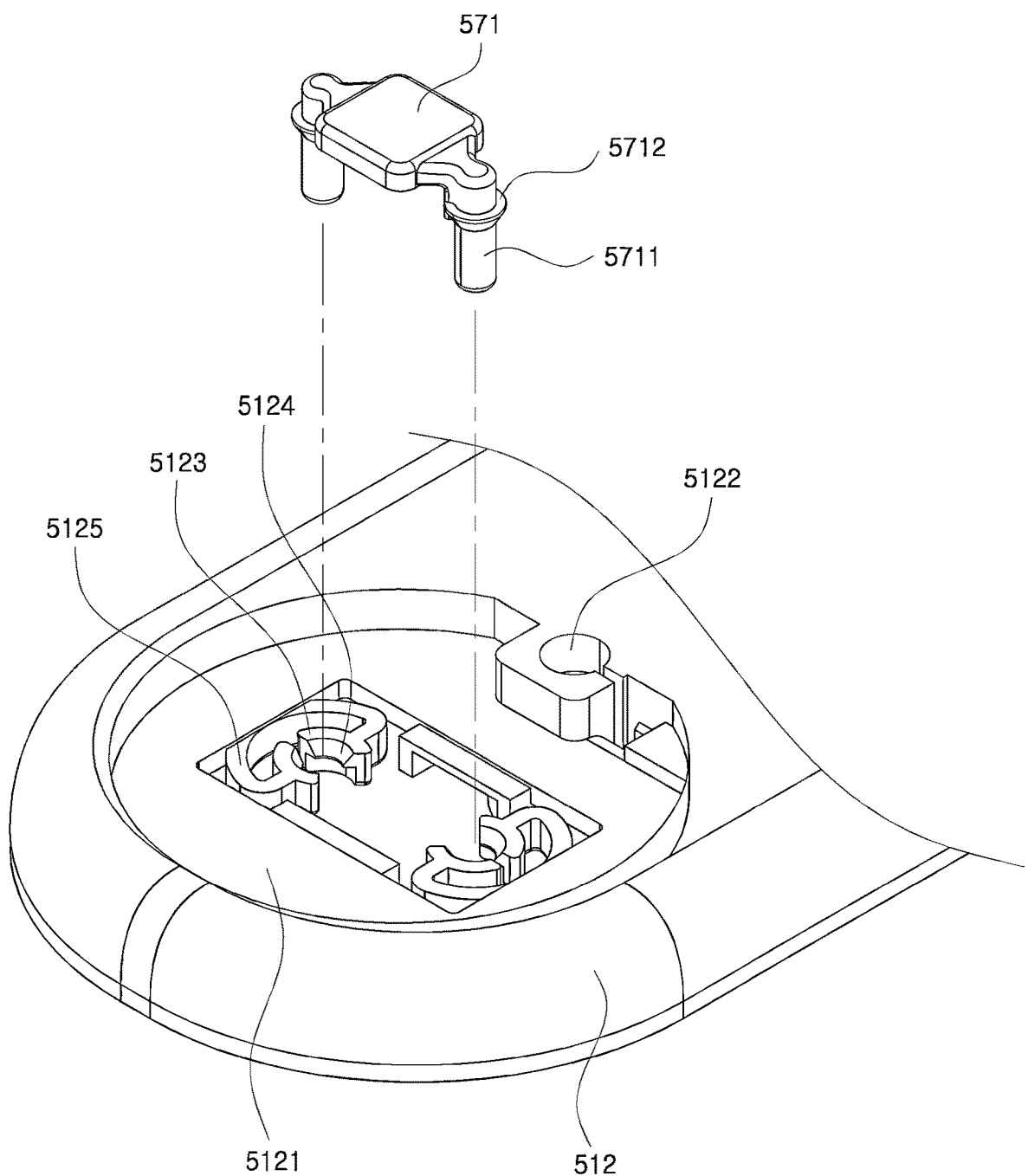
FIG. 31 is a perspective view of schematically illustrating detailed configuration of a pressurizing operation module according to an embodiment of the present disclosure.

For fixing the position of the movable pressurizing body (571), a protruding guide unit (5711) protruding along a movement direction of the movable pressurizing body (571) is formed at the movable pressurizing body (571) as illustrated in FIG. 31, and a locking hook (5712) may be formed at the outer circumferential surface of the protruding guide (5711). Additionally, an interlocking projection (5124) to which the locking hook (5712) of the protruding guide unit (5711) in a state that the movable pressurizing body (571) is moved in the pressurized direction may be formed at the housing (510). The position of the movable pressurizing body (571) may be fixed as the locking hook (5712) is interlockedly coupled to the interlocking projection (5124) as shown in FIG. 30.

In this embodiment, the interlocking projection (5124) may be formed at the sensor supporting unit (5121) of the housing (510), at least two guide fixing units (5123) separated to each other, formed along a circumferential direction and having a structure covering the protruding guide unit (5711) of the movable pressurizing body (571) are formed at the sensor supporting unit (5121) of the housing (510) as illustrated in FIG. 31, and the interlocking protrusion (5124) may be formed at each guide fixing unit (5123). Additionally, each guide fixing unit (5123) may be arranged in a structure being elastically supported by the elastic supporting unit (5125) which is configured to be elastically transformable.

Accordingly, during the process that the movable pressurizing body (571) is moved toward the pressurized direction the guide fixing unit (5123) is elastically transformed and makes the movement of the movable pressurizing body (571) smooth, after the movement of the movable pressuring body (571) is completed, the guide fixing unit (5123) is elastically returned and the locking hook (5712) is interlockedly coupled to the interlocking projection (5124), and because the guide fixing unit (5123) is elastically supported by the elastic supporting unit (5125), the interlocking coupling state between the locking hook (5712) and the interlocking projection (5124) is stably maintained.

Meanwhile, the sensor unit (520) may consist of the sensor body unit (522) and the sensor probe unit (521) as described above, and a pressure transforming unit (523) configured to be transformed by the pressurizing movement of the movable pressurizing body (571) and contacted to the electric contact point (531) of the PCB board (530) may be formed at the sensor body unit (522).

Figure 32:
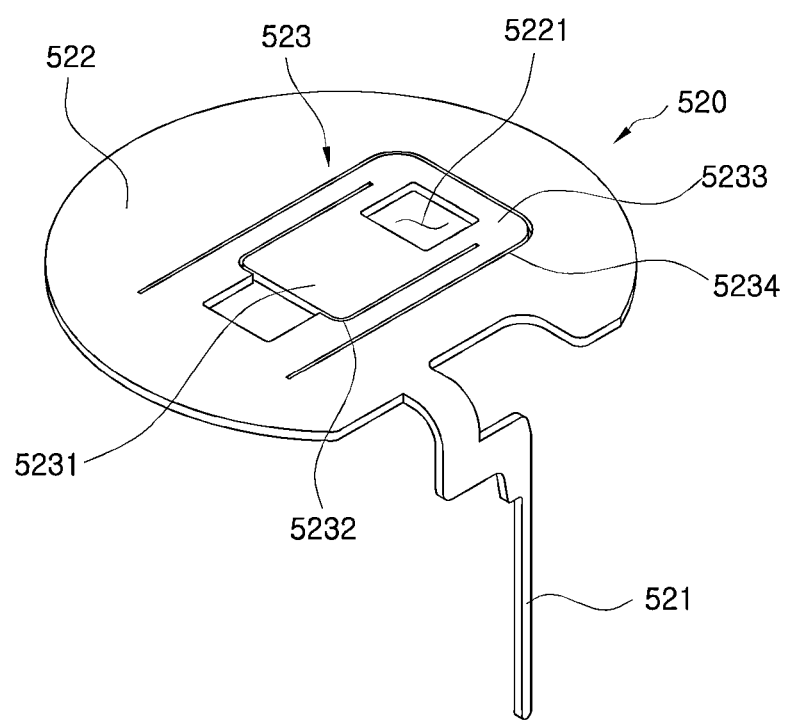
FIG. 32 is a perspective view of schematically illustrating detailed configuration of a sensor unit according to an embodiment of the present disclosure.

The pressure transforming unit (523) comprise a first cut area (5231) having a structure cut along a first cut line (5232) formed at the center section of the sensor body unit (522) as illustrated in FIG. 32, and the first cut area (5231) may be formed to be transformable by the pressure applied by the movable pressurizing body (571).

Additionally, the pressure transforming unit (523) further comprise a second cut section (5233) positioned at the center section of the sensor body unit (522) and having a structure cut along a second cut line (5234) formed at the outer section of the first cut line (5232), and the first cut area (5231) and the second cut area (5233) may be formed to be transformable by the pressure applied by the movable pressurizing body (571).

In this embodiment, the first cut line (5232) is formed as an partially opened structure in a closed loop, and the second cut line (5234) is formed to have an opened section at the position opposing to the opened section of the first cut line (5232) and formed in a closed-loop structure surrounding the opened section of the first cut line (5232).

Figure 33:
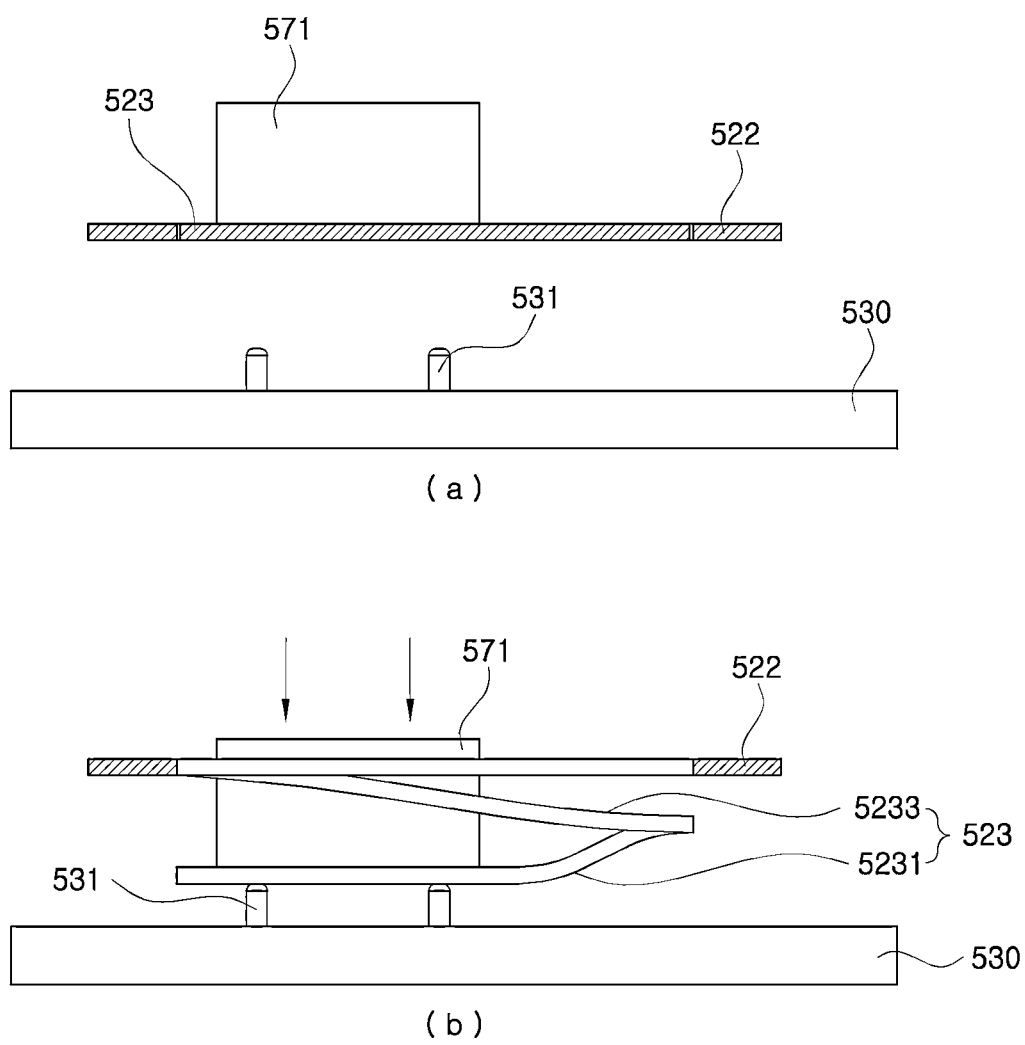
FIG. 33 is a view of conceptually illustrating a pressurizing operation state of a sensor unit according to an embodiment of the present disclosure.

If the movable pressurizing body (571) is operated by the pressure according to the structure described above, a first cut section (5231) of the pressure transforming unit (523) is downwardly elastically transformed as illustrated in FIGS. 33(*a*) and (*b*), then a second cut section (5233) formed at an outer section of the first cut are (5231) is downwardly elastically transformed sequentially, and therefore because the first cut section (5231) directly contacting the electric contact point (531) of the PCB board (530) contact the electric contact point (531) of the PCB board (530) in a relatively horizontal state, the contacting state to the electric contact point (531) of the sensor body unit (522) can be more stably maintained.

Meanwhile, at the PCB board (530), a plurality of electric contact points (531) electrically contacting the sensor body unit (522) may protrude toward the sensor body unit (522), and the protruding height of at least one of the plurality of electric contact points (531) may be higher than the rest.

Figure 34:
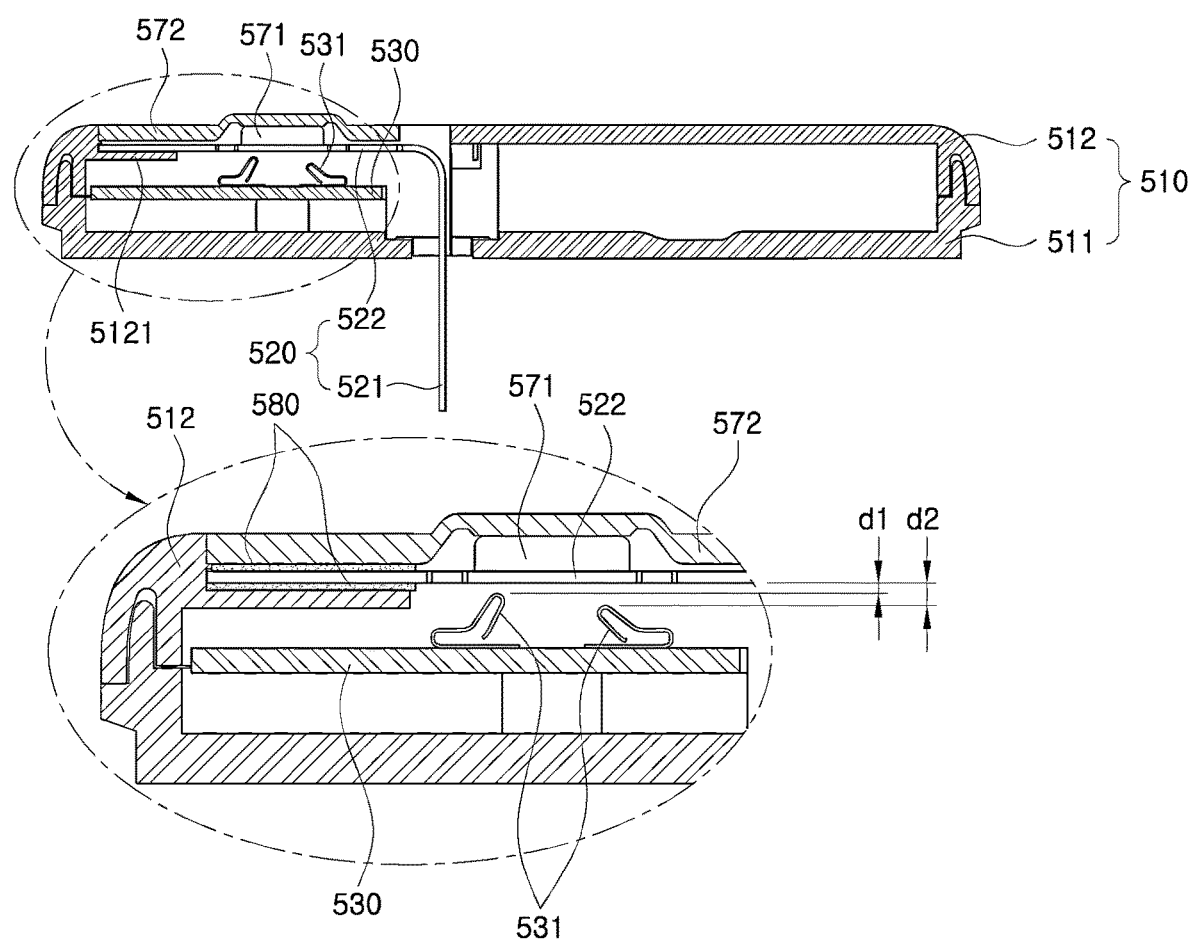
FIG. 34 is a view of conceptually illustrating arrangement relation between a sensor unit and an electrical contact point according to an embodiment of the present disclosure.

For example, when two electric contact points (531) are formed on the PCB board (530) as illustrated in FIG. 34, the protruding height of one of the electric contact points (531) is formed be higher than the other of the electric contact points (531), and therefore clearance distances d1, d2 are formed differently from each other.

By this arrangement structure, the contact of the sensor body unit (522) to the electric contact point (531) even without the pressure operation of the user due to the manufacture and assembly tolerance may be prevented.

Specifically, according to an embodiment of the present disclosure, in the housing (510), the sensor body unit (522) of the senor unit (520) and the electric contact point (531) of the PCB board are disposed to be separated from each other, but can contact each other by the pressure operation of the user. However, because the housing (531) may be formed in a very thin structure, it may be difficult of stably maintaining the separation state between the sensor body unit (522) and the electric contact point (531) in the housing (510). Specially, the sensor body unit (522) and the electric contact point (531) may be manufactured and distributed to customers in a state that the sensor body unit (522) and the electric contact point (531) contact each other by the manufacture and assembly tolerance and other reasons before the pressure operation of the user.

If the protruding height of at least one of the plurality of electric contact points (531) is higher that the rest of the electric contact points (531) as described above, only the electric contact point (531) having the highest protruding height may contact the sensor body unit (522) and the other electric contact points (531) may maintain a separation state from the sensor body nit (522). This is because the highest protruding contact point (531) can perform the function of upwardly supporting the sensor body unit (522). In this embodiment, the plurality of electric contact points (531) may be configured to elastically transformable and be formed to elastically protruding from the PCB board (530), and such an elastic force may perform the desired function of support and contact associated with the sensor body unit (522).

Even if the sensor body unit (522) and at least one of the electric contact points (531) contact each other but only one of the electric contact points (531) contacts the sensor body unit (522), the operation of the body attachable unit (20) is not initiated. Accordingly, the operation of the sensor unit (520), the wireless communication chip (540), and other components is not initiated, and the power supply by the battery (535) may not be initiated.

This operation initiation prevention function can result from simple means for setting the circuit pattern of the PCB board (530) to be activated only when all of the plurality of the electric contact points (531) contact the sensor body unit (522).

When the plurality of electric contact points (531) have different protruding heights from each other, the pressurizing operation module (570) may need to be formed so that the movement distance of the movable pressurizing body (571) can be greater than the separation distance between the lowest protruding electric contact point (531) among the plurality of the electric contact points (531) and the sensor body unit (522).

Although embodiments of configuration of the pressurizing operation module (570) operated by the pressure type with respect to the structure of contacting the sensor body unit (522) and the electric contact point (531) by the user's operation are described above, various types in addition to the pressure type may be implemented, and some exemplary configurations are described as follows.

Figure 35:
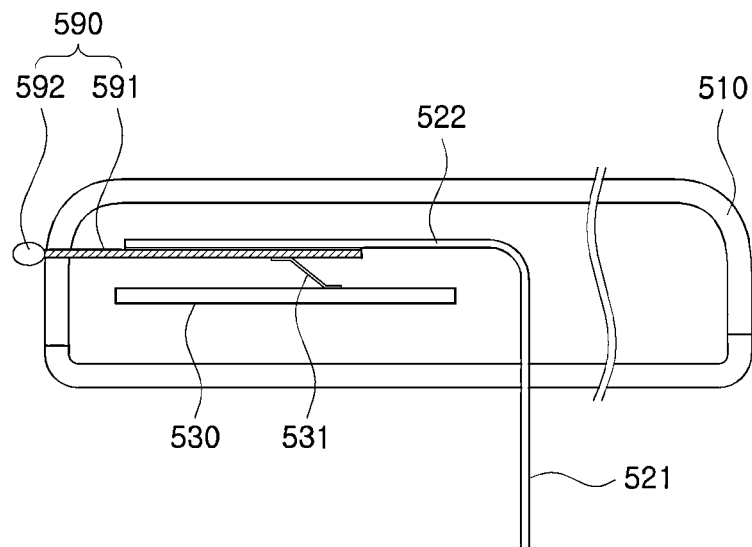
FIGS. 35 to 37 are views of conceptually illustrating various configurations of electrical contact points according to embodiments of the present disclosure.
Figure 35:
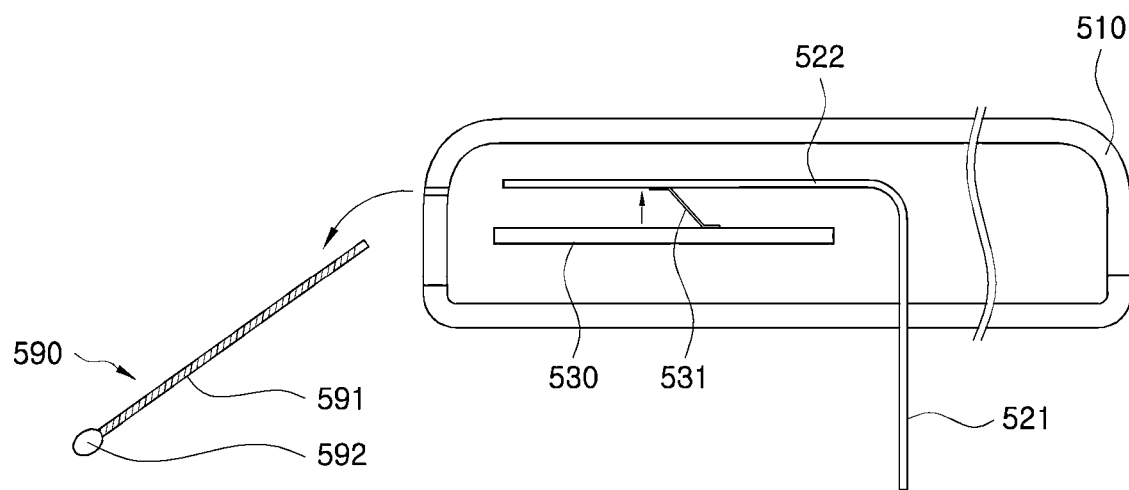
Figure 36:
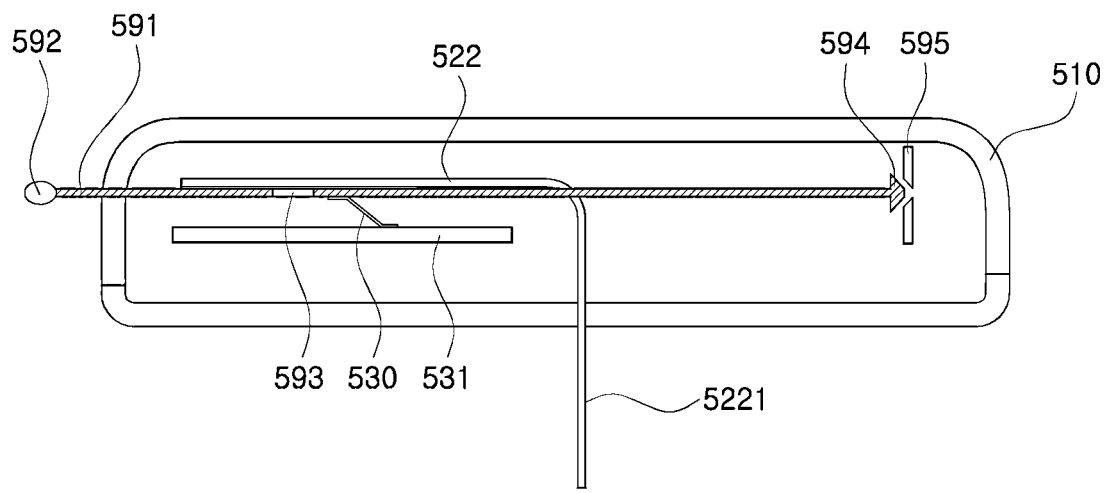
Figure 36:
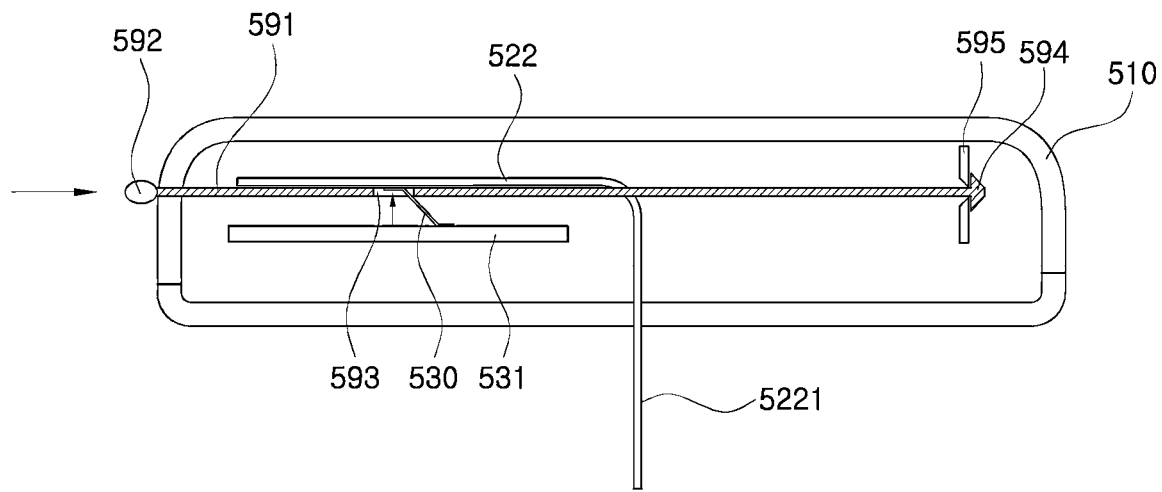
Figure 37:
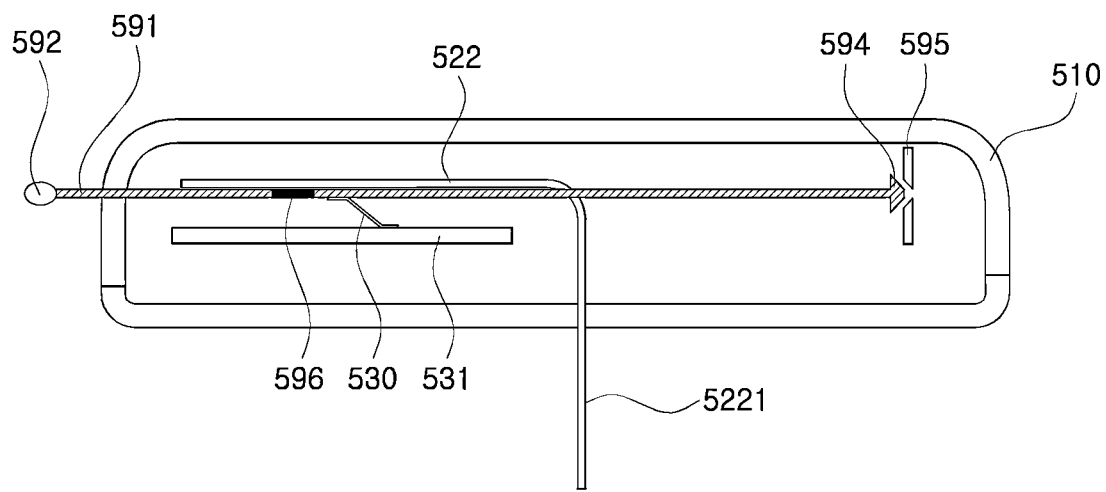
Figure 37:
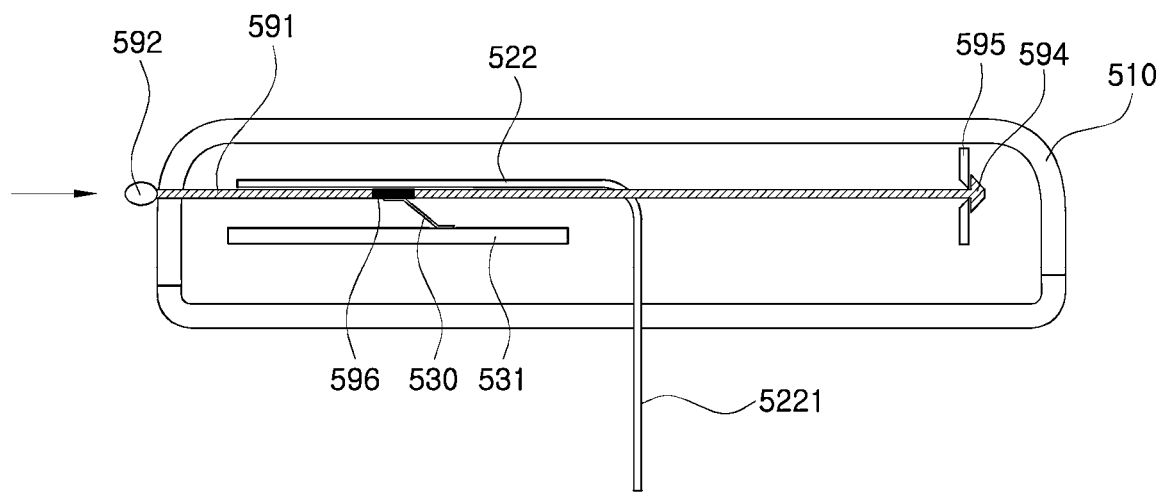

FIGS. 35 to 37 are conceptual views of various configuration of a contact point connection module according to embodiments of the present disclosure.

A contact point connection module (590) which is operated by the manipulation of the user so that the sensor body unit (522) and the electric contact point (531) of the PCB board (530) contact each other is illustrated in FIGS. 35 to 37, and this contact point connection module (590) may be configured to operate in a type that in a state that the contact point connection module (590) is positioned between the sensor body unit (522) and the electric contact point (531) of the PCB board (530) to block their contact the contact point connection module (590) may be moved by the operation of the user to release from blocking the contact between the sensor body unit (522) and the electric contact point (531) of the PCB board (530).

Specifically, the electric contact point (531) of the PCB board (530) is formed to elastically protrude in a direction that the electric contact point (531) can contact the sensor body unit (522), and as the contact point connection module (590) releases from blocking the contact between the sensor body unit (522) and the electric contact point (531) of the PCB board (530), the electric contact point (531) of the PCB board (530) is configured to be elastically moved by the elastic force and be contacted to the other end portion of the sensor unit (520).

In this embodiment, the contact point connection module (590) may be configured to comprise a movable plate (591) disposed between the sensor body unit (522) and the electric contact point (531) of the PCB board (530) and installed to be movable according to the operation of the user inside the housing as illustrated in FIG. 35.

As shown in FIG. 35(a), in the assembled state that the movable plate (591) is inserted into the inside of the housing (510), the movable plate (591) is positioned between the sensor body unit (522) and the electric contact point (531) to block the contact between the sensor body unit (522) and the electric contact point (531), and as illustrated in FIG. 35(b), if the movable plate (591) is moved in a direction of being extracted and removed from the housing (510) by the operation of the user, the electric contact point (531) is upwardly moved by the elastic force and contacted to the sensor body unit (522).

Meanwhile, as illustrated in FIG. 36, the movable plate (591) is installed to be movable from the first location to the second location by the operation of the user, and a penetrating hole (593) may be formed at one side of the movable plate (591) and the penetrating hole (593) is configured to pressurize the electric contact point (531) toward the PCB board (530) at the first location and release the pressurized state of the electric contact point (531) at the second location.

Accordingly, as shown in FIG. 36(a), in a state that the movable plate (591) is positioned at the first location inside the housing (510), the contact between the sensor body unit (522) and the electric contact point (531) is blocked by the movable plate (591), and as illustrated in FIG. 36(b), if the movable plate (591) is moved to the second location in the housing (510), the electric contact point (531) is elastically moved, penetrates the penetrating hole (593), and contact the sensor body unit (522) because the penetrating hole (593) of the movable plate (591) is positioned between the electric contact point (531) and the sensor body unit (510).

In this embodiment, a stopper unit (592) formed to limit a movable range of the movable plate (591) to between the first location and the second location may be formed at the movable plate (591).

Meanwhile, the movable plate (591) may be configured to be unable to return to the first location again so that the position of the movable plate (591) is fixed in a state that it is moved to the second location.

For example, a locking hook (594) is formed at one end portion of the movable plate (591), an interlocking projection (595) configured to be interlocked with the locking hook (594) in a state that the movable plate (591) is moved to the second location is formed in the housing (510), and as the locking hook (594) is interlockedly coupled to the interlocking projection (595), the position of the movable plate (591) is fixed to the second location.

Further, as illustrated in FIG. 37, a contact point connection unit (596) made of conductive material may be additionally installed to the movable plate (591). This may be configured in a structure that the contact point connection unit (596) is installed to a portion where the penetrating hole (593) of the movable plate (591) is formed, and the electric contact point (531) and the sensor body unit (522) are electrically connected and contacted to each other by the contact point connection unit (596) when the movable plate (591) is moved.

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. A body attachable device for continuous glucose measurement, the body attachable device configured to be attachable to a body by an applicator for the continuous glucose measurement, the body attachable device comprising:
   a housing, wherein a bottom surface of the housing is to contact a skin;
   a printed circuit board (PCB) including electric contact points and disposed inside the housing;
   a sensor disposed within the housing, wherein one end portion of the sensor outwardly protrudes from the bottom surface of the housing to be inserted into the body when the housing contacts the skin by a first operation, and an other end portion of the sensor unit is configured to be contacted to the electric contact points; and a contact point connecting module movably disposed between the sensor and the electric contact points to block contact between the sensor unit and the electric contact points, wherein the one end portion of the sensor and a needle are inserted into the body and the needle is extracted from the body based on the first operation, and wherein the contact point connecting module includes a movable plate configured to move to make a connection between the sensor and the electric contact points based on a second operation.

2. The body attachable device for the continuous glucose measurement of claim 1, the contact point connecting module is configured to release from blocking the contact between the other end portion of the sensor and the electric contact points by moving.

3. The body attachable device for the continuous glucose measurement of claim 2, wherein the electric contact points of the PCB elastically protrude in a direction contactable with the other end portion of the sensor, wherein the electric contact points of the PCB are configured to be elastically movable by elastic force to contact the other end portion of the sensor unit as the contact point connecting module releases from blocking the contact between the other end portion of the sensor and the electric contact points.

4. The body attachable device for the continuous glucose measurement of claim 3, wherein the movable plate movably disposed between the other end portion of the sensor and the electric contact points in the housing, the movable plate configured to be movable from a first location to a second location according to the second operation, wherein the contact point connecting module pressurizes the electric contact points toward the PCB at the first location and a penetrating hole is formed at one side of the movable plate to release from pressurizing the electric contact points at the second location.

5. The body attachable device for the continuous glucose measurement of claim 4, wherein the housing comprises a stopper configured to limit a movable range of the movable plate from the first location to the second location.

6. The body attachable device for the continuous glucose measurement of claim 4, wherein the movable plate is configured such that the movable plate is fixed in a second location after the movable plate is moved.

7. The body attachable device for the continuous glucose measurement of claim 6, wherein a locking hook is formed at one end portion of the movable plate, an interlocking projection configured to be interlocked with the locking hook when the movable plate is fixed in the second location is formed at the housing, and the movable plate is configured such that the position of the movable plate is fixed at the second location by interlockingly coupling the locking hook to the interlocking projection.

8. A body attachable device for continuous glucose measurement, the body attachable device configured to be attachable to a body by an applicator for the continuous glucose measurement, the body attachable device comprising:

a housing, wherein a bottom surface of the housing is to contact a skin;

a printed circuit board (PCB) including electric contact points and disposed inside the housing;

a sensor unit disposed within the housing, wherein one end portion of the sensor unit outwardly protrudes from the bottom surface of the housing to be inserted into the body when the housing contacts the skin, and an other end portion of the sensor unit is configured to be contacted to the electric contact points; and a contact point connecting module movably disposed between the sensor unit and the electric contact points to block contact between the sensor unit and the electric contact points, wherein the contact point connecting module comprises a movable plate movably disposed between the other end portion of the sensor unit and the electric contact points in the housing, the movable plate configured to be movable from a first location to a second location, wherein the contact point connecting module pressurizes the electric contact points toward the PCB at the first location and a penetrating hole is formed at one side of the movable plate to release from pressurizing the electric contact points at the second location.

9. The body attachable device for the continuous glucose measurement of claim 8, wherein the housing comprises a stopper configured to limit a movable range of the movable plate from the first location to the second location.

10. The body attachable device for the continuous glucose measurement of claim 8, wherein the movable plate is configured such that the movable plate is fixed in a second location after the movable plate is moved.

11. The body attachable device for the continuous glucose measurement of claim 8, the contact point connecting module is configured to release from blocking the contact between the other end portion of the sensor and the electric contact points by moving.

12. The body attachable unit for the continuous glucose measurement of claim 11, wherein the electric contact points of the PCB elastically protrude in a direction contactable with the other end portion of the sensor, wherein the electric contact points of the PCB are configured to be elastically movable by elastic force to contact the other end portion of the sensor as the contact point connecting module releases from blocking the contact between the other end portion of the sensor and the electric contact points.

* * * * *